United States Patent
Takahashi et al.

(10) Patent No.: US 7,749,240 B2
(45) Date of Patent: Jul. 6, 2010

(54) ULTRASONIC SURGICAL SYSTEM

(75) Inventors: Hiroyuki Takahashi, Tokyo (JP); Eiji Murakami, Tokyo (JP)

(73) Assignee: Olympus Corporation, Tokyo (JP)

( * ) Notice: Subject to any disclaimer, the term of this patent is extended or adjusted under 35 U.S.C. 154(b) by 1742 days.

(21) Appl. No.: 10/900,810

(22) Filed: Jul. 28, 2004

(65) Prior Publication Data

US 2005/0033201 A1 Feb. 10, 2005

(30) Foreign Application Priority Data

Aug. 7, 2003 (JP) .............................. 2003-288941
Mar. 22, 2004 (JP) .............................. 2004-082577

(51) Int. Cl.
*A61B 17/32* (2006.01)
*A61B 17/20* (2006.01)

(52) U.S. Cl. ........................................ 606/169; 604/22

(58) Field of Classification Search ................ 600/459; 601/2; 604/22; 606/1, 169, 171
See application file for complete search history.

(56) References Cited

U.S. PATENT DOCUMENTS

| 5,897,569 | A | 4/1999 | Kellogg et al. |
| 6,569,109 | B2 | 5/2003 | Sakurai et al. |
| 6,678,621 | B2 | 1/2004 | Stulen et al. |
| 2001/0039389 | A1 | 11/2001 | Sakurai et al. |
| 2002/0107538 | A1 | 8/2002 | Shibata et al. |
| 2002/0161385 | A1 | 10/2002 | Wiener et al. |
| 2005/0070800 | A1* | 3/2005 | Takahashi ................. 600/459 |

FOREIGN PATENT DOCUMENTS

| DE | 40 40 537 A1 | 8/1991 |
| EP | 1 199 047 A2 | 4/2002 |
| EP | 1 199 049 A1 | 11/2002 |
| JP | H04-158856 | 6/1992 |
| JP | 5-49647 | 3/1993 |
| JP | 2000-237204 | 9/2000 |
| JP | 2000-271140 | 10/2000 |
| JP | 2001-258089 | 9/2001 |
| JP | 2002-18353 | 1/2002 |

(Continued)

OTHER PUBLICATIONS

JP Office Action mulled Oct. 27, 2009, together with English translation.

(Continued)

*Primary Examiner*—Nicholas D Lucchesi
*Assistant Examiner*—Nathan R Price
(74) *Attorney, Agent, or Firm*—Scully, Scott, Murphy & Presser, P.C.

(57) ABSTRACT

An ultrasonic surgical system includes a handpiece including an ultrasonic transducer and a first storage unit; a probe connected to the ultrasonic transducer; a calculation unit; and a control unit. The first storage unit stores a first parameter relating to control of the ultrasonic transducer. The probe transmits ultrasonic vibrations output from the ultrasonic transducer to a treatment target, and includes a second storage unit storing a second parameter relating to control of the ultrasonic transducer. The calculation unit calculates a control parameter for controlling the ultrasonic transducer, based on both the first parameter and the second parameter. The control unit controls the ultrasonic transducer based on the control parameter.

4 Claims, 16 Drawing Sheets

FOREIGN PATENT DOCUMENTS

| | | |
|---|---|---|
| JP | 2002-177292 | 6/2002 |
| JP | 2002-186901 | 7/2002 |
| JP | 2002-209907 | 7/2002 |
| JP | 2003-061975 | 3/2003 |
| JP | 2003-305050 | 10/2003 |

OTHER PUBLICATIONS

JP Decision on Patent Grant dated Feb. 9, 2010, together with English translation.

* cited by examiner

FIG.7

| | DRIVING FREQUENCY | AMPLITUDE MAGNIFICATION RATE | PARAMETER OF VOLTAGE MULTIPLYING RATIO | VOLTAGE RATING | COIL PARAMETER | OUTPUT MODULATION PARAMETER | SUCTION PARAMETER |
|---|---|---|---|---|---|---|---|
| PARAMETER #1 | 47kHz | 10-FOLD | 1:5 | 150V | 5mH | NO | NO |
| PARAMETER #2 | 23.5kHz | 10-FOLD | 1:10 | 300V | 10mH | NO | NO |

FIG.8

| | DRIVING FREQUENCY | CURRENT AMPLITUDE RATE | PARAMETER OF VOLTAGE MULTIPLYING RATIO | VOLTAGE RATING | COIL PARAMETER | SUCTION APPLICABILITY PARAMETER |
|---|---|---|---|---|---|---|
| PARAMETER #3 | 47kHz | 10μm/A | 1:5 | 150V | 5mH | NO |
| PARAMETER #4 | 23.5kHz | 20μm/A | 1:10 | 300V | 10mH | NO |

FIG.9

| | DRIVING FREQUENCY | DRIVING CURRENT PARAMETER | PARAMETER OF VOLTAGE MULTIPLYING RATIO | VOLTAGE RATING | COIL PARAMETER | OUTPUT MODULATION PARAMETER | SUCTION PARAMETER |
|---|---|---|---|---|---|---|---|
| PARAMETER #1, #3 | 47kHz | 1.0A | 1:5 | 150V | 5mH | NONE | NONE |
| PARAMETER #1, #4 | | | ABNORMAL COMBINATION | | | | |
| PARAMETER #2, #3 | | | | | | | |
| PARAMETER #2, #4 | 23.5kHz | 0.5A | 1:10 | 300V | 10mH | NONE | NONE |

FIG.12

| IDENTI-FICATION | CHARACTERICTIC | DRIVING FREQUENCY | OUTPUT MODULATION | SUCTION |
|---|---|---|---|---|
| TYPE A | SCISSORS TYPE FOR ENDOSCOPE OPERATION | 47kHz | NO | NO |
| TYPE B | HOOK TYPE FOR ENDOSCOPE OPERATION | 47kHz | NO | NO |
| TYPE C | SCISSORS TYPE FOR CELIOTOMY OPERATION | 23.5kHz | NO | NO |
| TYPE D | SUCTION TYPE FOR ENDOSCOPE OPERATION | 23.5kHz | NO | YES |
| TYPE E | SUCTION TYPE FOR CELIOTOMY OPERATION | 23.5kHz | NO | YES |
| TYPE F | LITHOTRITE TYPE FOR CELIOTOMY OPERATION | 23.5kHz | YES | NO |

FIG.13

| IDENTI-FICATION | DRIVING FREQUENCY | SUCTION APPLICABILITY |
|---|---|---|
| TYPE G | 23.5kHz | NO |
| TYPE H | 47kHz | NO |
| TYPE I | 23.5kHz | YES |

FIG. 14

| DATA NO. | PROBE IDENTI-FICATION | HANDPIECE IDENTI-FICATION | DRIVING FREQUENCY | DRIVING CURRENT PARAMETER | PARAMETER OF VOLTAGE MULTIPLYING RATIO | VOLTAGE RATING | COIL PARAMETER | OUTPUT MODULATION PARAMETER | SUCTION PARAMETER |
|---|---|---|---|---|---|---|---|---|---|
| DATA #1 | TYPE A | TYPE G | ABNORMAL COMBINATION | | | | | | |
| DATA #2 | TYPE A | TYPE H | 47kHz | 0.7A | 1:10 | 300V | 5mH | NO | NO |
| DATA #3 | TYPE A | TYPE I | ABNORMAL COMBINATION | | | | | | |
| DATA #4 | TYPE B | TYPE G | ABNORMAL COMBINATION | | | | | | |
| DATA #5 | TYPE B | TYPE H | 47kHz | 0.7A | 1:5 | 150V | 5mH | NO | NO |
| DATA #6 | TYPE B | TYPE I | ABNORMAL COMBINATION | | | | | | |
| DATA #7 | TYPE C | TYPE G | 23.5kHz | 1.0A | 1:10 | 300V | 10mH | NO | NO |
| DATA #8 | TYPE C | TYPE H | ABNORMAL COMBINATION | | | | | | |
| DATA #9 | TYPE C | TYPE I | 23.5kHz | 1.0A | 1:10 | 300V | 5mH | NO | NO |
| DATA #10 | TYPE D | TYPE G | ABNORMAL COMBINATION | | | | | | |
| DATA #11 | TYPE D | TYPE H | ABNORMAL COMBINATION | | | | | | |
| DATA #12 | TYPE D | TYPE I | 23.5kHz | 0.7A | 1:5 | 150V | 5mH | NO | YES |
| DATA #13 | TYPE E | TYPE G | ABNORMAL COMBINATION | | | | | | |
| DATA #14 | TYPE E | TYPE H | ABNORMAL COMBINATION | | | | | | |
| DATA #15 | TYPE E | TYPE I | 23.5kHz | 1.0A | 1:10 | 300V | 5mH | NO | YES |
| DATA #16 | TYPE F | TYPE G | 23.5kHz | 1.0A | 1:10 | 300V | 10mH | YES | NO |
| DATA #17 | TYPE F | TYPE H | ABNORMAL COMBINATION | | | | | | |
| DATA #18 | TYPE F | TYPE I | 23.5kHz | 1.0A | 1:10 | 300V | 5mH | YES | NO |

ULTRASONIC SURGICAL SYSTEM

CROSS-REFERENCE TO RELATED APPLICATIONS

This application claims the benefit of priority of Japanese Patent Applications No. 2003-288941 filed on Aug. 7, 2003, and No. 2004-082577 filed on Mar. 22, 2004, and the entire disclosures of which are incorporated herein by reference.

BACKGROUND OF THE INVENTION

1) Field of the Invention

The present invention relates to an ultrasonic surgical system with which a surgical medical treatment such as an incision and a blood coagulation at a target such as a living tissue is operated, applying ultrasonic vibrations.

2) Description of the Related Art

An ultrasonic surgical system with which an incision or an excision is operated on a target such as a living tissue by ultrasonically vibrating a tip of a probe that is installed to an operating instrument while blood vessels and nerve tissue and the like are preserved has conventionally been developed. The ultrasonic vibrations of the ultrasonic surgical system are realized by drive controlling an ultrasonic transducer that is installed in a handpiece. Generally, it is preferable that the ultrasonic vibrations are controlled to drive at around a resonance frequency.

An example of such an ultrasonic surgical system is disclosed in Japanese Patent Application Laid-Open No. 2000-237204. The ultrasonic surgical system executes a PLL (Phase Locked Loop) control. A frequency of a signal to drive control the ultrasonic transducer is controlled to agree with the resonance frequency by comparing a phase difference between a driving current and a driving voltage provided to the ultrasonic transducer. The ultrasonic surgical system retrieves a resonance condition by providing a resonance frequency that is detected most lately when an abnormal driving is occurred.

Moreover, an example of an ultrasonic surgical system is disclosed in Japanese Patent Application Laid-Open No. 2002-209907. The ultrasonic surgical system stores a driving current, a maximum output voltage, a control mode, a maximum load point, and a frequency lock region in a nonvolatile memory such as an EEPROM. The nonvolatile memory is embedded in a cable of a handpiece. Generation of ultrasonic frequency is controlled based on parameters stored in the nonvolatile memory when the power is just turned on, or when a load that fluctuates the resonance frequency is given.

In the field of medical treatment such as an endoscope surgical operation, an ultrasonic surgical system has been used choosing combinations of various kinds of handpieces having particular driving characteristics and various operating instruments that include probes having various shapes depending on a case. Therefore, there has been a demand for an appearance of an ultrasonic surgical system that drives various kinds of handpieces efficiently in a resonance condition with only one control system, and that outputs desirable ultrasonic vibrations from various kinds of probes. In other words, an improvement in a general versatility of the control system to the handpiece and an improvement in a general versatility of the handpiece to the probe are both required.

SUMMARY OF THE INVENTION

An ultrasonic surgical system according to one aspect of the present invention includes a handpiece including an ultrasonic transducer and a first storage unit; a probe connected to the ultrasonic transducer; a calculation unit; and a control unit. The first storage unit stores a first parameter relating to control of the ultrasonic transducer. The probe transmits ultrasonic vibrations output from the ultrasonic transducer to a treatment target, and includes a second storage unit storing a second parameter relating to control of the ultrasonic transducer. The calculation unit calculates a control parameter for controlling the ultrasonic transducer, based on both the first parameter and the second parameter. The control unit controls the ultrasonic transducer based on the control parameter.

An ultrasonic surgical system according to another aspect of the present invention includes a handpiece including an ultrasonic transducer and a first identifier; a probe connected to the ultrasonic transducer; a storage unit storing a control parameter for controlling the ultrasonic transducer; a first control unit; and a second control unit. The first identifier contains vibrator identification information to identify the ultrasonic transducer. The probe transmits ultrasonic vibrations output from the ultrasonic transducer to a treatment target, and includes a second identifier containing probe identification information to identify the probe. The control parameter is obtained based on the vibrator identification information and the probe identification information. The first control unit matches the handpiece and the vibrator identification information determined from the first identifier, matches the probe and the probe identification information determined from the second identifier, and reads, from the storage unit, the control parameter corresponding to the vibrator identification information determined and the probe identification information determined. The second control unit controls the ultrasonic transducer based on the control parameter read by the first control unit.

A probe according to still another aspect of the present invention is connected to an ultrasonic transducer, and transmits ultrasonic vibrations output from the ultrasonic transducer to a treatment target. The probe also includes a storage unit that stores a second parameter relating to control of the ultrasonic transducer, and that is arranged in a portion of the probe. The portion corresponds to a node of a standing wave produced by the ultrasonic transducer.

The other objects, features, and advantages of the present invention are specifically set forth in or will become apparent from the following detailed description of the invention when read in conjunction with the accompanying drawings.

BRIEF DESCRIPTION OF THE DRAWINGS

FIG. 7 is a table of probe output parameters;

FIG. 8 is a table of vibrator output parameters;

FIG. 9 is a table of control parameters that are derived from the probe output parameters and the vibrator output parameters;

FIG. 12 is a table that provides a characteristic and parameters of each probe according to the second embodiment;

FIG. 13 is a table of handpiece parameters according to the second embodiment of the present invention;

FIG. 14 is a table of control parameters that are stored in the ultrasonic surgical system according to the second embodiment;

DETAILED DESCRIPTION

Exemplary embodiments of an ultrasonic surgical system according to the present invention are explained in detail with reference to accompanying drawings.

Figure 1:
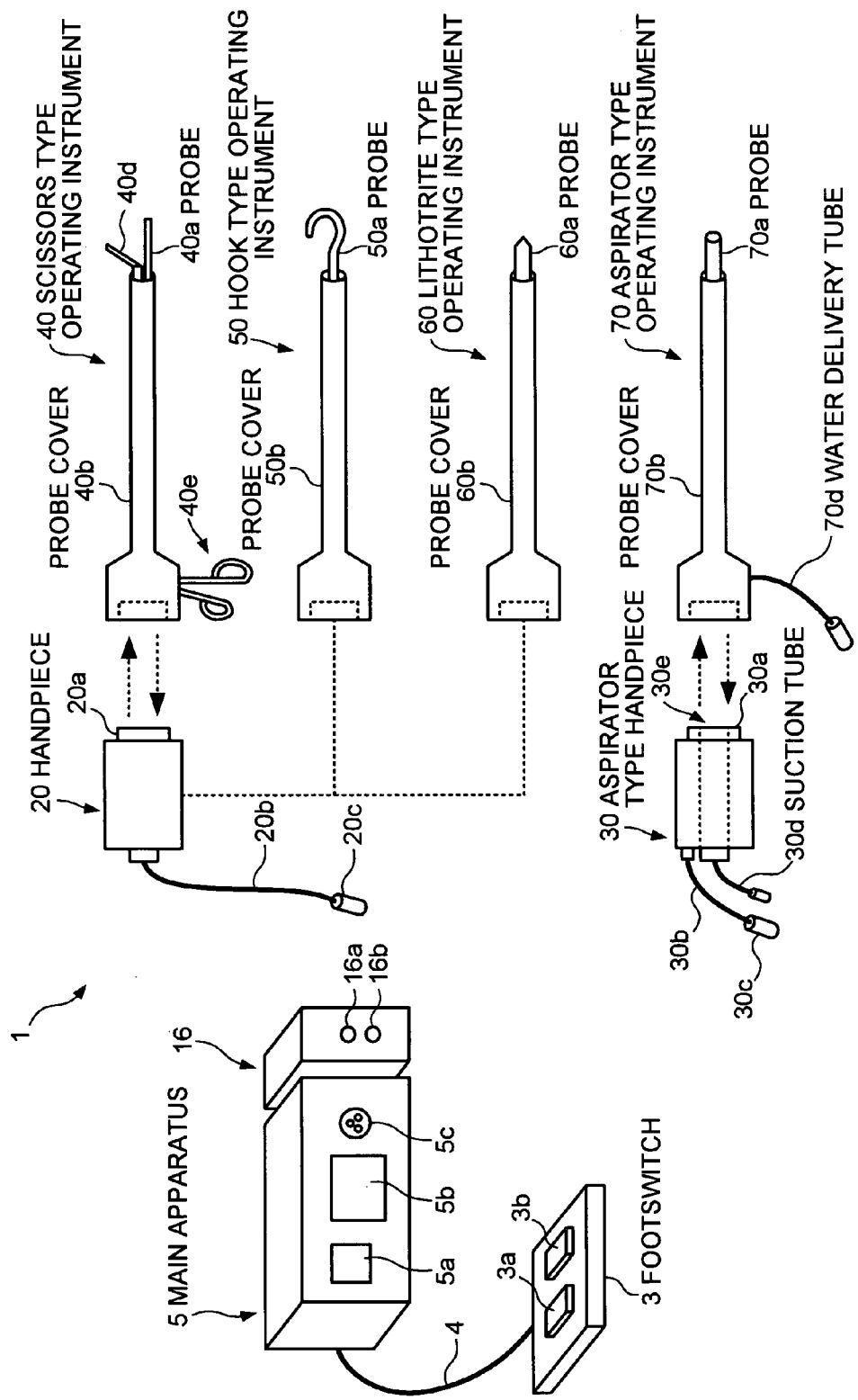
FIG. 1 is a schematic diagram of an ultrasonic surgical system according to a first embodiment of the present invention.

FIG. 1 is a schematic diagram of a configuration of an ultrasonic surgical system according to a first embodiment of the present invention. As shown in FIG. 1, an ultrasonic surgical system 1 includes a main apparatus 5 and a footswitch 3. The main apparatus 5 includes a power switch 5a, a display unit 5b, and a connector 5c. The footswitch 3 includes pedals 3a, 3b. The footswitch 3 is electrically connected to the main apparatus 5 through a cable 4. A handpiece 20 that includes an ultrasonic transducer composed of a piezoelectric ceramic and the like is also electrically connected to the main apparatus 5. The handpiece 20 includes a cable 20b that has an end connected to the ultrasonic transducer and the other end that includes a plug 20c. The handpiece 20 and the main apparatus 5 are connected to each other through the cable 20b by plugging the plug 20c into the connector 5c.

The handpiece 20 includes a joint 20a to detachably connect a desirable operating instrument. The desirable operating instrument to be selected includes a scissors type operating instrument 40, a hook type operating instrument 50, and a lithotrite type operating instrument 60. The desirable operating instrument is connected to the handpiece 20 by screwing onto the joint 20a or by fitting the joint 20a with springs and the like. A probe of the connected operating instrument should maintain a contact with the ultrasonic transducer. For example, a scissors type operating instrument 40 is connected to the handpiece 20 detachably onto the joint 20a with screws in such a manner that a probe 40a maintains a contact with the ultrasonic transducer in the handpiece 20.

The scissors type operating instrument 40 includes the probe 40a that transmits desirable ultrasonic vibrations to a target. The probe 40a is formed with titanium or a titanium alloy and the like. The probe 40a is detachably inserted in a probe cover 40b that includes a jaw 40d and a grip 40e. With the scissors type operating instrument 40, a medical treatment is carried out by manipulating the grip 40e to nip a target with both the probe 40a and the jaw 40d during the desirable ultrasonic vibrations are being transmitted to the probe 40a.

A hook type operating instrument 50 includes a probe 50a. The probe 50a is formed with titanium or a titanium alloy. The probe 50a is inserted into a probe cover 50d. With the hook type operating instrument, a medical treatment is carried out by catching a target with a hook-shaped part of the probe 50a during the desirable ultrasonic vibrations are being transmitted to the probe 50a.

A lithotrite type operating instrument 60 includes a probe 60a. The probe 60a is formed with titanium and a titanium alloy. The probe 60a is detachably inserted into a probe cover 60b. With the lithotrite type operating instrument 60, a medical treatment is carried out by pressing a tip of the probe 60a to a target during the desirable ultrasonic vibrations are being transmitted to the probe 60a.

Each operating instrument, including an aspirator type operating instrument 70 described later, should be formed with a material that endures a rigorous sterilization such as an autoclave.

A suction processing device 16 can be arranged in the main apparatus 5 as required. The suction processing device 16 includes a water supply opening 16a and a suction opening 16b. The suction processing device 16 has functions of conveying perfusion solution such as physiological salt solution, and sucking an emulsified target and the like. The aspirator type handpiece 30 is electrically connected to the main apparatus 5, and the aspirator type operating instrument 70 is connected to the aspirator type handpiece 30. The ultrasonic surgical system 1 can operate a suction treatment when the aspirator type handpiece 30 and the aspirator type operating instrument 70 are connected to the suction processing device 16.

The aspirator type handpiece 30 includes an ultrasonic transducer and a cable 30b. The cable has an end connected to the ultrasonic transducer inside and the other end that includes a plug 30c. The handpiece 30 is connected to the main apparatus 5 by plugging the plug 30c into the connector 5c. The aspirator type handpiece 30 includes a joint 30a, a suction tube 30d, and an opening 30e. A desirable operating instrument is connected to the joint 30a. The opening 30e links the joint 30a and the suction tube 30d. The suction processing device 16 and the aspirator type handpiece 30 are connected to each other through the suction tube 30d that is connected to the suction opening 16b.

The aspirator type operating instrument 70 includes a probe 70a to transmit desirable ultrasonic vibrations to a target, and to suck the emulsified target. The probe 70a is formed with titanium and a titanium alloy. The probe 70a includes an opening (not shown) inside that opens through in the direction of length. The probe 70a is detachably inserted in a probe cover 70b. The aspirator type operating instrument 70 also includes a water delivery tube 70d that links to an end of the probe cover 70b, which is a side that the medical treatment is carried out. The suction processing device 16 and the aspirator type operating instrument 70 are connected to each other by plugging the water delivery tube 70d to the water supply opening 16a.

The aspirator type handpiece 30 has a function of attaching a desirable operation instrument. The aspirator type operation instrument 70 is detachably connected to the aspirator type handpiece 30 onto the joint 30a, for example with screws, in such a manner that the probe 70a maintains a contact with the ultrasonic transducer in the aspirator type handpiece 30.

Each type of handpiece, including the handpiece 20 and the aspirator type handpiece 30, is categorized into various types according to frequency characteristics of each of the ultrasonic transducers, and is selectively connected to the main apparatus 5 depending on a use. Moreover, within a range compatible with the frequency characteristics, each type of operation instrument, including the scissors type operation instrument 40, the hook type operation instrument 50, or the lithotrite type operating instrument 60, may be connected to the handpiece 20 or the aspirator type handpiece 30 selectively, and operation instruments such as a knife type and a drill type (not shown) may also be connected to the handpiece 20 or the aspirator type handpiece 30. In other words, various types of handpieces can be selectively connected to the main apparatus 5, and various kinds of operation instruments can be selectively connected to each handpiece.

A connecting condition of a desirable handpiece and an operating instrument in the ultrasonic surgical system 1 is explained below in detail. A case in which the scissors type operating instrument 40 is connected to the handpiece 20 is explained below. Although the first embodiment exemplifies various kinds of combinations composed of the operating instruments such as the hook type operating instrument 50, the lithotrite type operating instrument 60, and the aspirator type operating instrument 70 other then the scissors type operating instrument 40 and the handpieces such as the handpiece 20 and the aspirator type handpiece 30, it is not to be limited to these elements.

Figure 2:
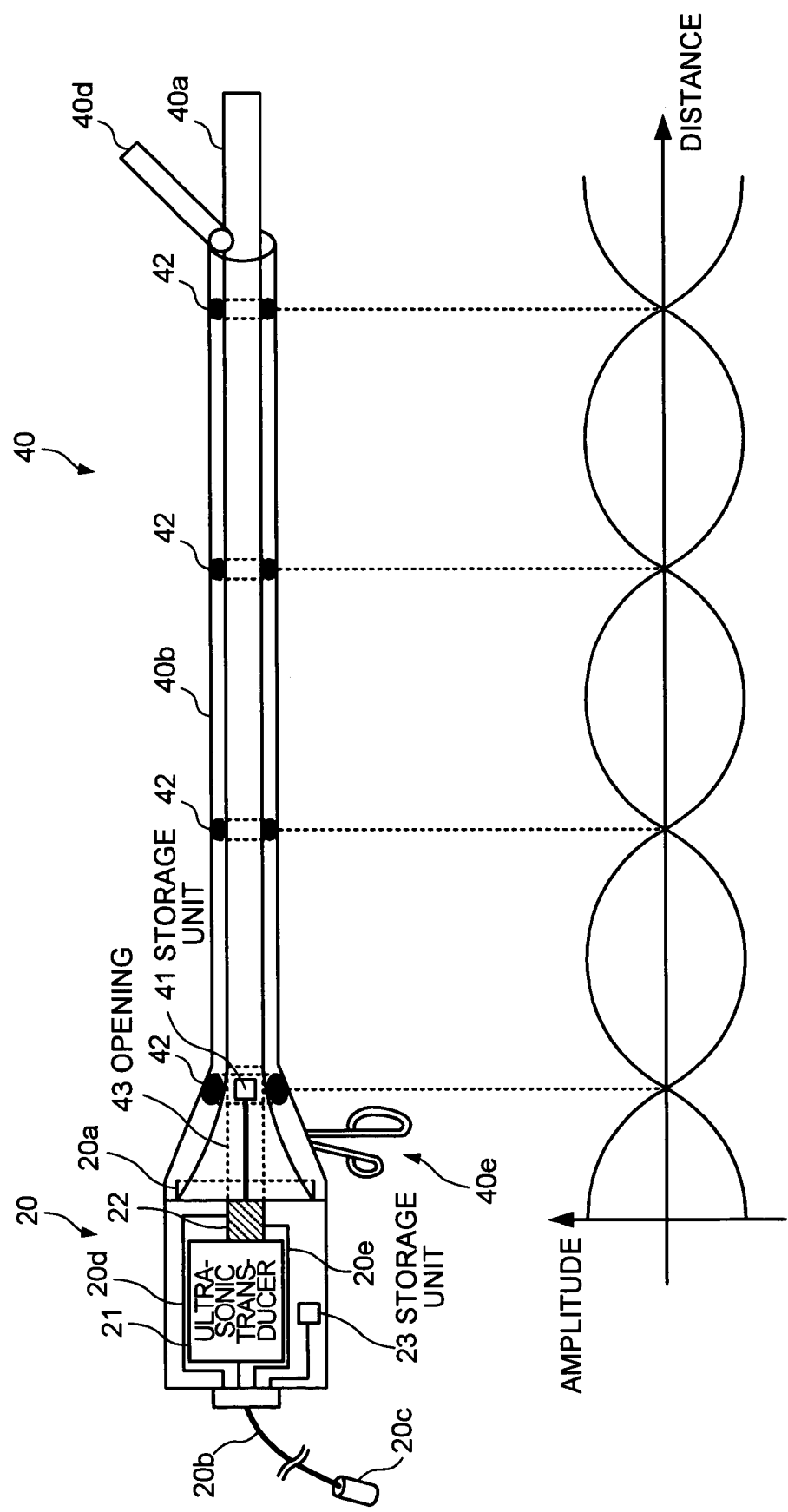
FIG. 2 is a diagram of a handpiece and a probe that are connected to each other.

FIG. 2 is a diagram that indicates the state in which the handpiece 20 and the scissors type operating instrument 40 are detachably connected to each other. In FIG. 2, a waveform of desirable ultrasonic vibrations that are transmitted to the probe 40*a* of the scissors type operating instrument 40 is also exemplified.

As shown in FIG. 2, the probe 40*a* is fastened to the handpiece 20 onto a fastening part 22 with screws at a joint 20*a*. Thus, the probe 40*a* and the probe cover 40*b* are detachably connected to the handpiece 20. In this case, an ultrasonic transducer 21 in the handpiece 20 has contact with the probe 40*a* to transmit the desirable ultrasonic vibrations to the probe 40*a*.

The handpiece 20 includes the ultrasonic transducer 21 and a storage unit 23. The ultrasonic transducer 21 and a storage unit 23 are electrically connected to the main apparatus 5 through the cable 20*b* when the plug 20*c* is plugged into the connector 5*c*. The probe 40*a* includes an opening 43 near the fastening part 22. The storage unit 43 is disposed inside the opening 43. The storage unit 41 is electrically connected to the main apparatus 5 when the probe 40*a* is fastened to the handpiece 20 with screws, and the plug 20*c* is plugged into the connector 5*c*. The arrangement of the storage unit 41 is explained later.

The scissors type operating instrument 40 includes a desirable number of seal materials 42. The seal material 42 is arranged at a desirable position around the probe 40*a*, and thus keeps the probe 40*a* detachably in the probe cover 40*b*.

When the ultrasonic transducer 21 outputs a desirable ultrasonic vibrations to the probe 40*a*, a longitudinal wave of a standing wave that propagates the ultrasonic vibrations is generated at the probe 40*a*. As shown in FIG. 2, a phase of the waveform of the standing wave corresponds to a position of the probe 40*a*. The standing wave exhibits a node at a portion in which the seal material 42 supports the probe 40*a*, and exhibits an antinode at a tip of the probe 40*a*. In other words, the seal material 42 is arranged in such a manner that the standing wave exhibits the antinode at the tip of the probe 40*a* so that the probe 40*a* transmits the ultrasonic vibrations certainly to the tip.

The number of the seal material 42 should only be enough to securely support the probe 40*a* in the probe cover 40*b*. It is preferable that the seal material 42 is arranged at a regular interval. This enables to inhibit occurrence of phenomena such as a deflection and a bend of the probe 40*a* caused by the ultrasonic vibrations, therefore, realizes reduction of the damage to the probe 40*a*, and transmission of stable ultrasonic vibrations. An O-ring and the like that are formed with various kinds of resins and a rubber can be applied as the seal material 42.

Figure 3:
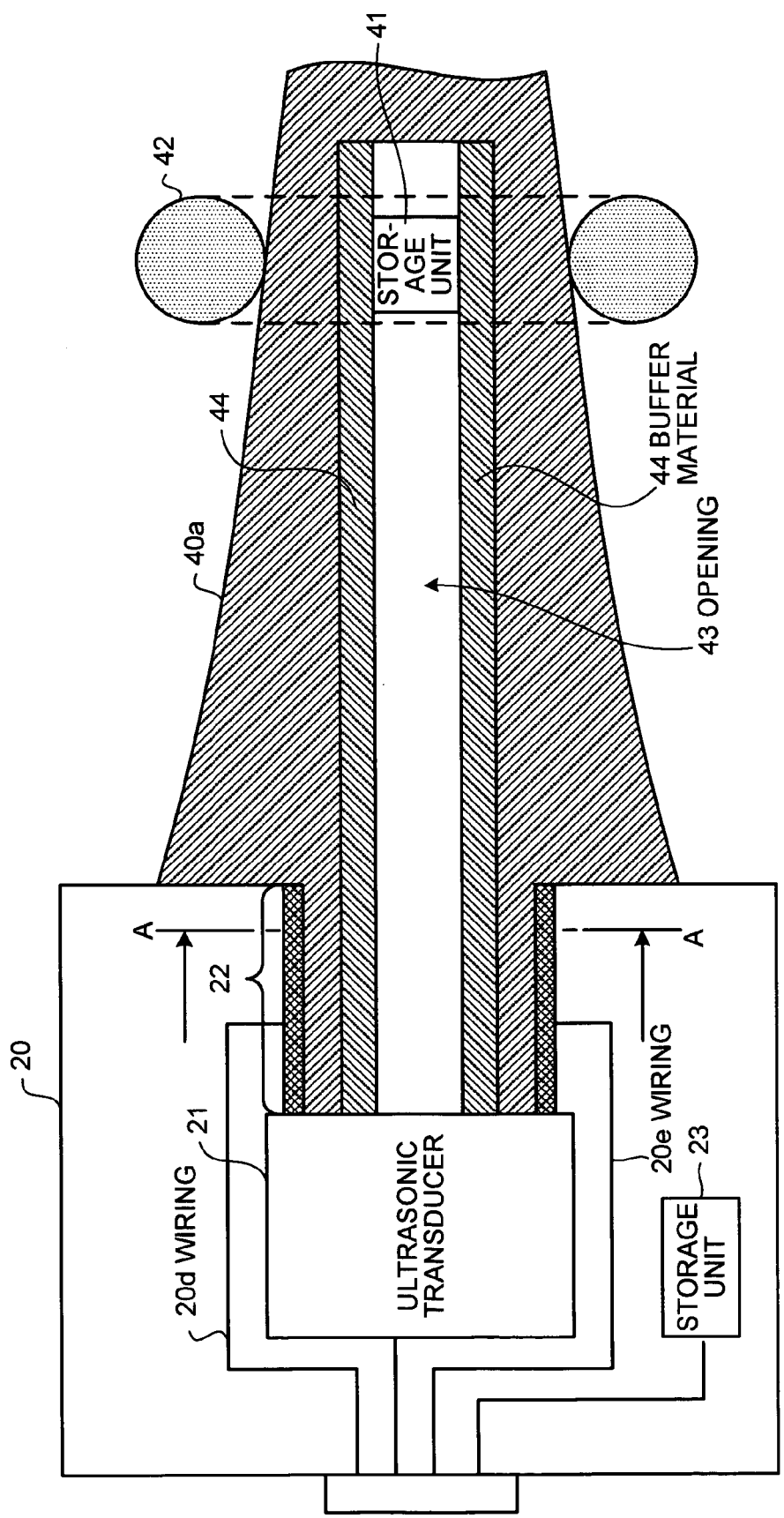
FIG. 3 is a schematic diagram for explaining condition of the probe and the handpiece that are connected to each other, and disposition of a storage unit in the probe.

FIG. 3 is a cross-section that exemplifies a condition of the probe 40*a* and the handpiece 20 clamped with screws, and an arrangement of a storage unit 41. As shown in FIG. 3, the probe 40*a* is connected to the handpiece 20 at the fastening part 22 with screws. Thus, the probe 40*a* is fixed to the ultrasonic transducer 21. The probe 40*a* also includes an opening 43 inside and a buffer material 44. The opening 43 reaches from the fastening part 22 to at least the portion in which the seal material 42 is placed. The buffer material 44 covers the surface inside the opening 43, and is prepared so as not to block the transmission of the ultrasonic vibrations.

The storage unit 41 is disposed in the opening 43 at a position inside the seal material 42, and is fixed to the wall of the opening 43 through the buffer material 44. In other words, the storage unit 41 is arranged in the portion that corresponds to the node of the standing wave. The probe 40*a* transmits the ultrasonic vibrations having the longitudinal wave by the standing wave. The node of the standing wave is where the least displacement is caused, and the most stress is applied by the ultrasonic vibrations. Therefore, it is possible to prevent a malfunction such as damage of the storage unit 41 or a brake in a cable that is caused by the ultrasonic vibrations by disposing the storage unit 41 in the position that corresponds to the node of the standing wave.

The buffer material 44 is formed with an elastic body such as a rubber or various kinds of resins such as of vinyl family or of urethane family. The buffer material 44 holds the storage unit 41 and ease the stress to the storage unit 41. Furthermore, a wiring (not shown) that electrically connects the storage unit 41 and the handpiece 20 is laid in the buffer material 44 so that the stress on the wiring is lessened to prevent a malfunction such as a break in a cable. The storage unit 41 is electrically connected to wirings 20*d*, 20*e* in the handpiece 20 through both the wiring that is laid in the buffer material 44 and the fastening part 22.

Furthermore, if the wiring laid in the buffer material or the storage unit 41 is formed with a flexible base, it is possible to further reduce the stress concentrated at the wiring or the storage unit 41. It is preferable that the storage unit 41 is disposed near the center of the cross-section of the probe 40*a* to inhibit occurrence of phenomena such as a deflection and a bend of the probe 40*a*, and to reduce the damage to the probe 40*a*.

Figure 4:
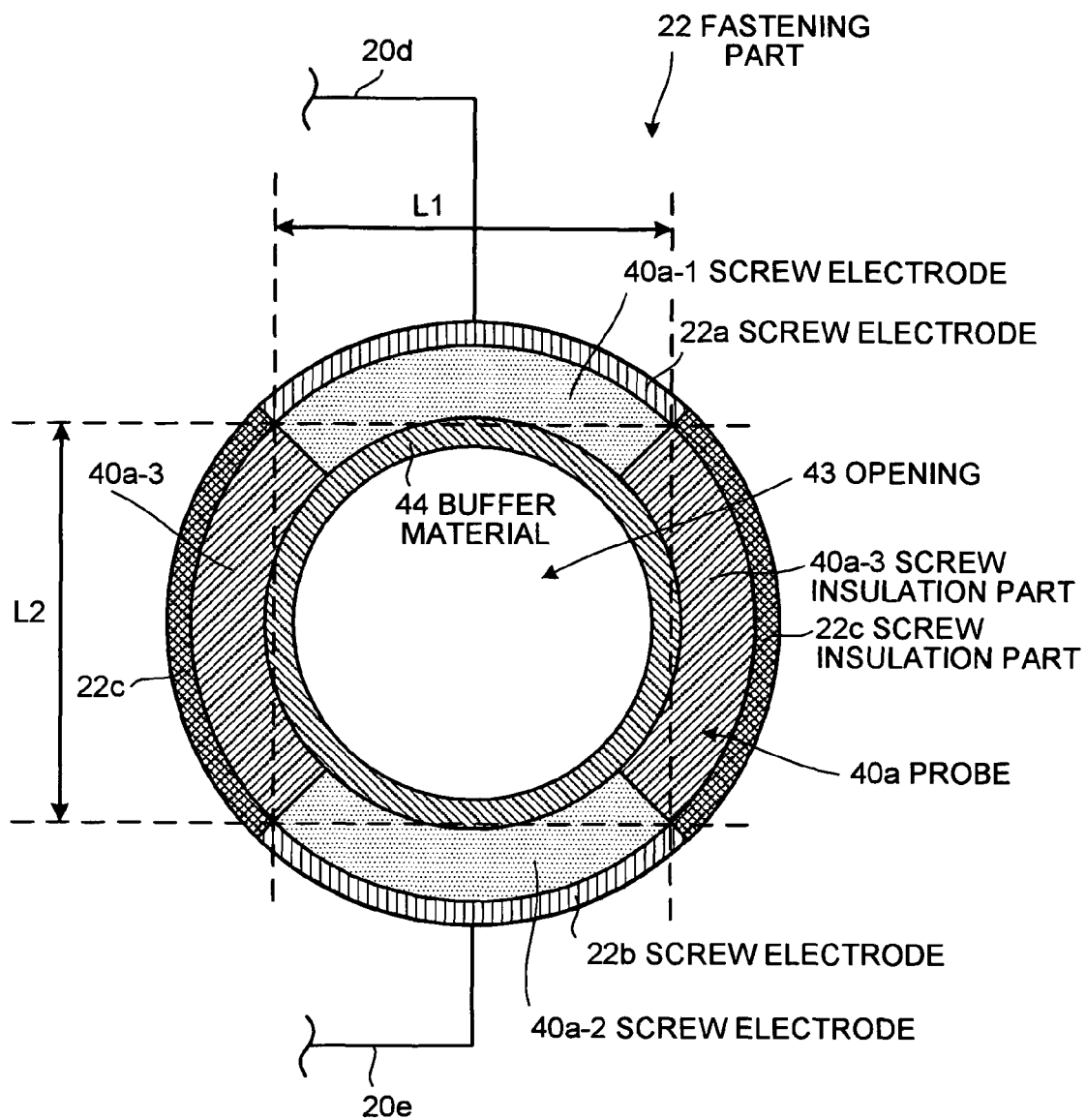
FIG. 4 is a cross-section of a fastening part taken along a line A-A shown in FIG. 3.

As shown in FIG. 4, the buffer material 44 is prepared so as to cover the inner surface of the probe 40*a* in the opening 43. The fastening part 22 includes screw parts of the probe 40*a* and screw parts of the handpiece 20. The screw parts of the probe 40*a* include screw electrodes 40*a*-1, 40*a*-2 and a screw insulation part 40*a*-3. The screw parts of the handpiece include screw electrodes 22*a*, 22*b*, and a screw insulation part 22*c*. The probe 40*a* and the handpiece 20 are connected by fastening both the screw parts.

The screw electrode 40*a*-1 is insulated from the screw electrode 40*a*-2 by the screw insulation part 40*a*-3. Likewise, the screw electrode 22*a* is insulated from the screw electrode 22*b* by the screw insulation part 22*c*. The storage unit 41 is electrically connected to the screw electrodes 40*a*-1 and 40*a*-2 through the wiring (not shown) laid in the buffer material 44. Moreover, the screw electrodes 22*a* and 22*b* are electrically connected to the wirings 20*d* and 20*e* in the handpiece respectively. Therefore, the storage unit 41 is electrically connected to the wiring 20*d* through the screw electrodes 40*a*-1, 40*a*-2, and the screw electrode 22*a* when the probe 40*a* and the handpiece 20 are securely fastened, and is electrically connected to the wiring 20*e* through the other wiring laid in the buffer material 44, screw electrode 40*a*-1, and the screw electrode 22*b*. The screw electrodes 40*a*-1, 40*a*-2 and the screw electrodes 22*a*, 22*b* function as two signal lines to communicate information between the storage unit 41 and the main apparatus 5 grounding to the earth.

The screw electrodes 40*a*-1, 40*a*-2 and the screw electrodes 22*a*, 22*b* are formed in such a manner that a maximum width L1 of the screw electrodes 40*a*-1, 40*a*-2 shown in FIG. 4 is smaller than a minimum space L2 of the screw electrodes 22*a*, 22*b*. This enables the screw electrode 40*a*-1 to be electrically connected to the screw electrode 22*a* without contact with both the screw electrodes 22*a*, 22*b* at the same time.

Figure 5:
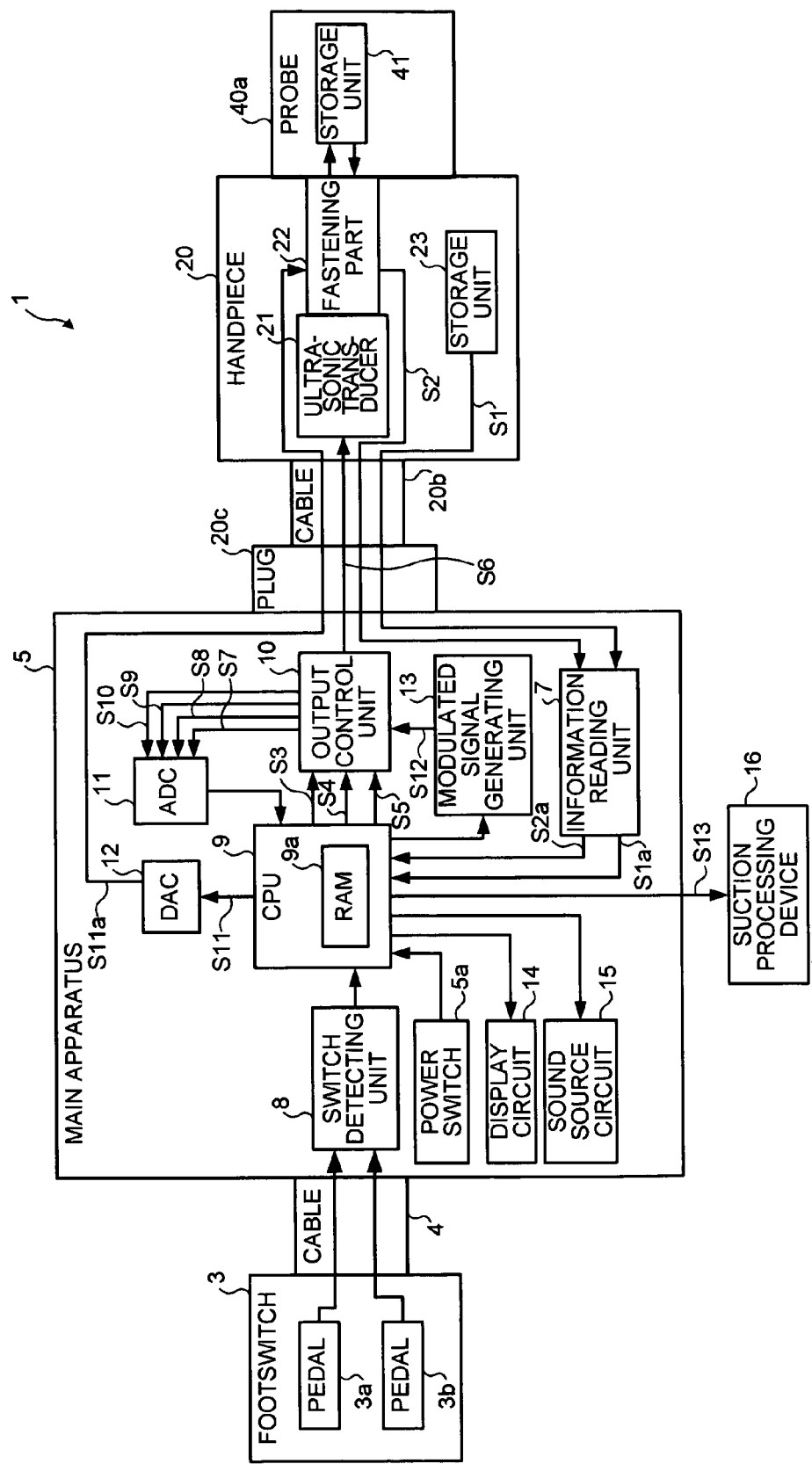
FIG. 5 is a block diagram of a system configuration of the ultrasonic surgical system according to the first embodiment.

A system configuration of the ultrasonic surgical system according to the first embodiment of the present invention is explained in detail. FIG. 5 is a block diagram of the system configuration of the ultrasonic surgical system. As shown FIG. 5, the ultrasonic surgical system 1 includes the main apparatus 5. The footswitch 3 is connected to the main apparatus 5 through the cable 4, and the handpiece 20 is connected to the main apparatus 5 through both the cable 20*b* and the plug 20*c*. The probe 40*a* is connected to the handpiece 20 at the fastening part 22 with screws. Moreover, the suction processing device 16 is connected to the main apparatus 5.

The main apparatus 5 includes an information reading unit 7 to which the power switch 5*a* and the storage units 23, 41 are electrically connected, a switch detecting unit 8 to which the pedals 3*a*, 3*b* are electrically connected, a CPU (Central Processing Unit) 9, and an output control unit 10 that is electrically connected to the ultrasonic transducer 21. Moreover, the main apparatus 5 includes an AD converter (ADC) 11, a DA converter (DAC) 12, a modulated signal generating unit 13, a display circuit 14, and a sound source circuit 15. The CPU 9 controls the information reading unit 7, the switch detecting unit 8, the output control unit 10, the modulated signal generating unit 13, the display circuit 14, and the sound source circuit 15. The power switch 5*a* is connected to the CPU 9. The ADC 11 is connected to both the CPU 9 and the output control unit 10. The DAC 12 is connected to both the CPU 9 and the storage unit 41. The CPU 9 is electrically connected to the suction processing device 16, and controls the suction processing device 16.

The information reading unit 7 is electrically connected to the storage units 23, 41, and reads the vibrator output parameters in the storage unit 23 and the probe output parameters in the storage unit 41 when the power is turned on by the power switch 5*a*. The information reading unit 7 converts each of the vibrator output parameters and the probe output parameters into predetermined digital codes, and then transmits each of the digital codes to the CPU 9. The information reading unit 7 receives vibrator output information S1 from the storage unit 23 as the vibrator output parameters, and transmits the vibrator output information S1*a* as information converted into predetermined digital codes to the CPU 9. Moreover, the information reading unit 7 receives probe output Information S2 as the probe output parameters from the storage unit 41, and transmits the probe output Information S2*a* as information converted into predetermined digital codes to the CPU 9. The vibrator output parameters here are parameters that relate to ultrasound output characteristics of the ultrasonic transducer 21. The vibrator output parameters include a driving frequency of the ultrasonic transducer 21, a current amplitude rate, voltage multiplying ratio parameters, a voltage rating, inductor parameters, and the like. The probe output parameters are parameters related to ultrasound output characteristics in the probe 40*a*. The probe output parameters include a driving frequency of the probe 40*a*, an amplitude magnification rate, voltage multiplying ratio parameters, a value of a voltage rating, inductor parameters, and the like.

The driving frequency is a parameter that corresponds to a reference frequency for a frequency sweep process to detect a resonance frequency. The current amplitude rate and the amplitude magnification rate are driving current setting parameters to calculate driving current parameters that set a value of the driving current to output the ultrasonic vibrations having desirable amplitude, and the voltage multiplying ratio parameters are parameters that set the voltage multiplying ratio of the driving voltage that depends on impedance characteristics of the ultrasonic transducer and the probe. The voltage rating is a parameter that sets a maximum output voltage of a signal to control the ultrasound output. The inductor parameters are parameters that correspond to a reference inductance value to set an inductance value of a parallel inductor by selecting a value of the parallel inductor.

The storage unit 41 may store output modulation parameters and suction parameters. The output modulation parameters determine whether the output modulation process is performed in the ultrasound output control. The suction parameters determine whether a suction process is performed by the suction processing device 16. The information reading unit 7 reads the output modulation parameters and the suction parameters from the storage unit 41 as one of the probe output parameters. Furthermore, the storage unit 23 may store suction applicability parameters that determine whether the suction process is applicable. The information reading unit 7 reads the suction applicability parameters form the storage unit 23 as one of the vibrator output parameters.

A rewritable nonvolatile memory such as an EPROM and an EEPROM can be used as the storage units 23, 41. It is preferable that an information communication mode between the storage units 23, 41 and the information reading unit 7 is a serial communication because this inhibits increase of the number of wirings.

The switch detecting unit 8 is set up to read, at all times, each information of switch on or switch off that is input from the pedals 3*a*, 3*b* in the footswitch 3. When the switch-on information is input from the pedals 3*a*, 3*b*, the switch detecting unit 8 transmits a signal that requests to start the predetermined ultrasound output control to the CPU 9. When the switch-off information is input from the pedals 3*a*, 3*b*, the switch detecting unit 8 transmits a signal that requests to stop the predetermined ultrasound output control to the CPU 9. For example, if the switch-on information from the pedal 3*a* relates to a detection of the resonance frequency, and the ultrasound output control (output setting control) that sets the driving current and the driving voltage, the switch detecting unit 8 transmits an instruction signal to start the output setting control based on the switch-on information from the pedal 3*a*, or transmits an instruction signal to stop the output setting control, which is being executed, based on the switch-off information from the pedal 3*a*. If the switch-on information from the pedal 3*b* relates to the ultrasound output control (output driving control) with the resonance frequency, the driving current, and the driving voltage that are predetermined, the switch detecting unit 8 transmits an instruction signal to start the output driving control based on the switch-on information from the pedal 3*b*, or transmits an instruction signal to stop the output driving control, which is being executed, based on the switch-off information from the pedal 3*b*.

When the power is turned on by the switch 5a, the CPU 9 transmits a signal to control a reading process of the vibrator output parameters and the probe output parameters to the information reading unit 7, and receives the vibrator output information S1a and the probe output Information S2a from the information reading unit 7. The CPU 9 calculates control parameters for the output setting control based on the vibrator output information S1a and the probe output Information S2a. The CPU 9 includes a RAM 9a. The RAM 9a stores the control parameters calculated. The control parameters include the driving frequency of the ultrasonic transducer 21, the driving current parameters, the voltage multiplying ratio parameters, the voltage rating, the inductor parameters, and the like.

When the CPU 9 receives the instruction signal to start the output setting control from the switch detecting unit 8, the CPU 9 reads the control parameters required for the output setting control from RAM 9a, and transmits the control parameters read to the output control unit 10. For example, the CPU 9 reads the driving frequency, the driving current parameters, the voltage multiplying ratio parameters, the voltage rating, and the inductor parameters from the RAM 9a as the control parameters required, and transmits PLL control information S3, voltage control information S4, and inductor setting information S5 to the output control unit 10. The PLL control information S3 corresponds to the driving frequency and the driving current parameters. The voltage control information S4 corresponds to the voltage multiplying ratio parameters and the voltage rating. The inductor setting information S5 corresponds to the inductor parameters.

The CPU 9 includes the ROM (not shown) that stores various data, and various processes by the CPU 9 are achieved by executing the program in the ROM.

Figure 6:
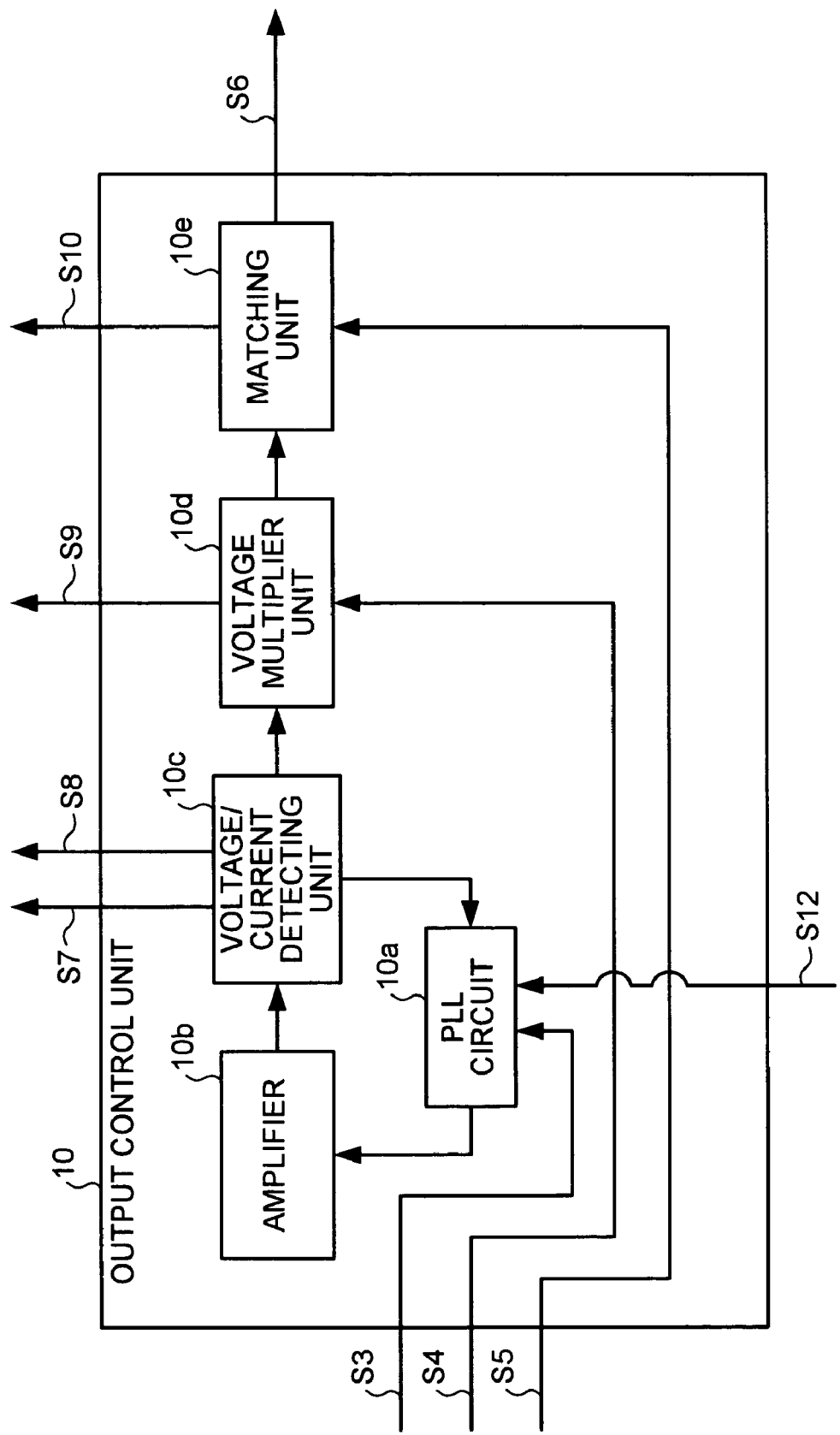
FIG. 6 is a block diagram of a schematic configuration of the output control unit shown in FIG. 5.

FIG. 6 is a block diagram of a schematic configuration of the output control unit 10. As shown in FIG. 6, the output control unit 10 includes the PLL circuit 10a, an amplifier 10b, a voltage/current detecting unit 10c, a voltage multiplier 10d, and a matching unit 10e. The PLL circuit 10a, the amplifier 10b, and the voltage/current detecting unit 10c are connected sequentially to make a loop. The voltage/current detecting unit 10c is connected to the voltage multiplier 10d, and the voltage multiplier 10d is connected to the matching unit 10e. The PLL circuit 10a is connected to the CPU 9 and the modulated signal generating unit 13. The voltage/current detecting unit 10c, the voltage multiplier 10d, and the matching unit 10e are connected to the CPU 9 through the ADC 11. The matching unit 10e is also connected to the handpiece 20 through the plug 20c and the cable 20b.

The PLL circuit 10a is realized with a well-known phase-locked circuit that includes a phase comparator and a voltage-controlled oscillator (VCO). The PLL circuit 10a detects a phase difference of a voltage and a current based on a signal that indicates each phase of the voltage and the current that are detected by the voltage/current detecting unit 10c. The PLL circuit then detects a resonance frequency at which the phase difference becomes zero. When the output control unit 10 receives PLL control information S3 from the CPU 9, the PLL circuit 10a executes the frequency sweep process to obtain vibrations at the resonance frequency, and creates an ultrasound output signal. In the frequency sweep process, the driving frequency in the PLL control information S3 is used as a reference frequency. When the resonance frequency is detected, the PLL circuit 10a executes the PLL control that controls each phase difference of the voltage and the current detected to become zero, and maintains the vibrations at the resonance frequency. The PLL circuit 10a also executes a negative feedback control, using the driving current parameter in the PLL control information S3 as a reference value, to make the reference value and the current value of the ultrasound output signal agree. Each of the control described above enables the PLL circuit 10a to transmit the ultrasound output signal that includes the resonance frequency at a desirable current value.

The ultrasound output signal is received by the voltage/current detecting unit 10c after the amplification of the power is carried out by the amplifier 10b. The voltage/current detecting unit 10c detects signals that indicate each of the phases of the voltage and the current in the ultrasound output signals, and transmits each of the signals to the PLL circuit 10a. Thus, the feedback loop of the PLL circuit 10a is realized, and the PLL circuit 10a executes the PLL control and the negative feedback. The voltage/current detecting unit 10c transmits the ultrasound output signal for which the amplification of the power is carried out to the voltage multiplier 10d. When the resonance frequency of the ultrasonic transducer 21 is detected, the voltage/current detecting unit 10c detects the resonance frequency and the driving current in the ultrasound output signal, and transmits the driving frequency information S7 that corresponds to the resonance frequency and the driving current information S8 that corresponds to the driving current to the CPU 9.

The voltage multiplier 10d is realized with an insulation transformer that transmits the power by a mutual induction between the parallel inductors. This enables the insulation between the electrical potential of the ultrasonic surgical system 1 and the electrical potential of a patient. When the output control unit 10 receives the voltage control information S4 from the CPU 9, the voltage multiplier 10d sets the voltage multiplying ratio based on the voltage multiplying ratio parameters in the voltage control information S4. The voltage multiplier 10d executes a voltage multiplication process to multiply the voltage in the ultrasound output signal to the desirable driving voltage. The voltage multiplier 10d then transmits the ultrasound output signal to the matching unit 10e. This enables a match of the impedance that is appropriate for the ultrasonic transducer 21 and the probe 40a. The voltage multiplier 10d also sets a maximum output voltage in the voltage multiplication process based on the voltage rating, and controls to keep the driving voltage in the ultrasound output signal below the maximum output voltage. This prevents an electrical breakdown of the ultrasonic transducer 21 and mechanical breakdown of both the ultrasonic transducer 21 and the probe 40a. If the driving voltage exceeds the maximum output voltage, the voltage multiplier 10d adjusts the voltage multiplying ratio to make the driving voltage lower than the maximum output voltage. Furthermore, the voltage multiplier 10d detects the voltage multiplying ratio after the voltage multiplication process or the adjustment, and transmits the voltage multiplying ratio information S9 that corresponds to the voltage multiplying ratio to the CPU 9.

The matching unit 10e is connected to the parallel inductor (not shown) that is arranged in the handpiece 20. The matching unit 10e has functions of selecting an inductor value, and setting an inductance value of the parallel inductor. The parallel inductor provides the ultrasonic transducer 21 with an inductive power that is generated by the ultrasound output signal. When the output control unit 10 receives the inductor setting information S5 from the CPU 9, the matching unit 10e sets the inductor value based on the inductor parameters in the inductor setting information S5, and prepares an environment in which the phase difference of each signal at the input/output unit is likely to become zero. This inhibits an attenuation of the signals such as a reflection phenomenon at the parallel inductor, and enables an efficient transmission of the ultrasound output signal. The matching unit 10e transmits the ultrasound output signal S6 to the parallel inductor as the ultrasound output signal that is received from the voltage multiplier 10d. Thus, the inductive power is provided to the ultrasonic transducer 21 by the ultrasound output signal S6 to generate the desirable ultrasonic vibrations. The matching unit 10e transmits matching inductor information S10 to the CPU 9 as parameters that correspond to the inductance value.

On the other hand, the CPU 9 receives the digital signals of the driving frequency information S7, the driving current information S8, the voltage multiplying ratio information S9, and the matching inductor information S10 from the output control unit 10 through the ADC 11, and stores in the RAM 9a as updated information of the control parameters. The CPU 9 updates the parameters that correspond to the updated information in the RAM 9a. The CPU 9 also transmits an instruction signal that outputs information indicating a state possible to output the ultrasonic vibrations at the resonance frequency to the display circuit 14 and the sound source circuit 15. The display circuit 14 displays such the state in the display unit 5b shown in FIG. 1 based on the instruction signal. The sound source circuit 15 outputs beeps and the like to indicate such the state based on the instruction signal.

The CPU 9 may transmit an instruction signal to output the updated information (for example, the driving frequency and the value of the driving current) in the control parameter described above to the display circuit 14, and the display circuit 14 may display the updated information in the display unit 5b.

Thus, an operator can recognize that the ultrasonic transducer 21 can be driven at the resonance condition by confirming the display contents in the display unit 5b or the sound by the sound source circuit 15. When the operator switches off the pedal 3a, the switch detecting unit 8 detects the switch-off information from the pedal 3a, and transmits an instruction signal to stop the output setting control to the CPU 9. The CPU 9 controls the output control unit 10 to stop the output setting control based on the instruction signal.

Moreover, upon receiving the instruction signal to stop the output setting control, the CPU 9 transmits parameter update information S11 as the probe output parameters that correspond to the latest control parameters in the RAM 9 to the DAC 12. The DAC 12 converts the parameter update information S11 into analog forms, and then transmits to the storage unit 41 to update the probe output parameters. Thus, the storage unit 41 stores the latest parameters to drive the probe 40a at the resonance condition, and the information reading unit 7 reads the latest parameters from the storage unit 41. The CPU 9 may transmit the parameter update information S11 also to the storage unit 23 as the vibrator output parameters that correspond to the latest control parameters in the RAM 9a to update the vibrator output parameters. The CPU 9 may update both the vibrator output parameters and the probe output parameters.

The operator switches on the pedal 3b in the footswitch 3 when a medical treatment is to be operated. The switch detecting unit 8 detects the switch-on information, and transmits an instruction signal 9 to start the output driving control to the CPU9. The CPU 9 transmits the updated information of the control parameters stored in the RAM 9a to the output control unit 10 based on the instruction signal. The output control unit 10 executes a control to output the ultrasound output signal of the desirable driving current and the desirable driving voltage based on the updated information, and transmits the ultrasound output signal S6 to the handpiece 20. The ultrasound output signal S6 is transmitted to the parallel inductor (not shown) that is arranged in the handpiece 20 Thus, the inductive power is generated and provided to the ultrasonic transducer 21. The ultrasonic transducer 21 outputs the desirable ultrasonic vibrations with the provided power. The ultrasonic vibrations are transmitted to the probe 40a through the fastening part 22, and the medical treatment can be carried out with the probe 40a. Thus, the output driving control described above is achieved.

When the medical treatment that is to be stopped, the operator should switch off the pedal 3b. The switch detecting unit 8 detects the switch-off information from the pedal 3b, and transmits the instruction signal to stop the output driving control to the CPU 9. The CPU 9 controls the output control unit 10 to stop the output driving control based on the instruction signal.

An abnormal information reading can be caused by a bad connection of the probe 40a to the handpiece 20 or the bad connection of the handpiece 20 to the main apparatus 5. If the information reading unit 7 fails to read the vibrator output information S1 or the probe output Information S2, the CPU 9 detects such the abnormal information reading. An abnormal combination can be caused by an incompatible combination of the handpiece and the operating instrument. If the driving at the resonance condition or a desirable medical treatment fails to be achieved due to such the abnormal combination, the CPU 9 detects the abnormal combination. When the abnormal information reading or the abnormal combination is detected, the CPU 9 controls the output control unit 10 to prohibit the output setting control or the output driving control. The CPU 9 also controls the display circuit 14 and the sound source circuit 15 to output a display or a sound to notify the occurrence of the abnormal information reading or the abnormal combination. Thus a use prohibition process is carried out.

The abnormal information reading is detected within a predetermined period of time after the power is turned only when the CPU 9 fails to receive the vibrator output information S1a or the probe output Information S2a from the information reading unit 7. The abnormal combination is detected based on the compatibility of each of the parameters, such as the driving frequency and the suction, in the vibrator output information S1a and the probe output Information S2a.

For example, if a probe having a driving frequency f1, for example of 47 kilohertz (kHz) is connected to a handpiece having a driving frequency FIG. 2, for example of 23.5 kHz, the driving frequencies f1, f2 are too different to create the ultrasound output signal in the resonance frequency. Therefore, the driving frequencies f1, f2 are incompatible, and correspond to the abnormal combination. Moreover, if a probe that is of suction applicable, such as the probe 70a of the aspirator type operating instrument 70, is connected to a handpiece that is of suction inapplicable, such as the handpiece 20, the suction parameters (suction process to be performed) and the suction applicability parameters (suction inapplicable) are incompatible. Therefore, this case corresponds to the abnormal combination described above.

When the lithotrite type operating instrument 60 is connected to the handpiece 20, output modulation parameters that indicate an existence of an output modulation is stored as the probe output parameters in the storage unit (not shown) in the probe 60a of the lithotrite type operating instrument 60. The output modulation parameters are included in the probe output Information S2. When the information reading unit 7 receives the probe output Information S2, the information reading unit 7 transmits the probe output Information S2a that is the probe output Information S2 converted into digital forms to the CPU 9. The CPU 9 calculates the control parameters based on the vibrator output information S1a and the probe output Information S2a, and stores the control parameters in the RAM 9a. The control parameters include the output modulation parameters.

The CPU 9 controls the modulated signal generating unit 13 to output a modulation signal to modulate the frequency of the ultrasound output signal of the output control unit 10 based on the output modulation parameters. It is preferable that the frequency of the modulation signal is adequately small compared to the driving frequency.

The modulated signal generating unit 13 transmits the modulated signal S12 to the output control unit 10 under the control of the CPU 9. The PLL circuit 10a receives the modulated signal S12. The PLL circuit 10a creates the ultrasound output signal with a modulated frequency by executing the frequency sweep process based on the driving frequency and the modulated signal S12 that are provided in the PLL control information S3. The ultrasound output signal with the modulated frequency corresponds to an intermitted wave of the ultrasound output signal S6. The desirable longitudinal and transverse vibrations can be simultaneously transmitted to the probe 60a by transmitting the ultrasound output signal with the modulated frequency to the ultrasonic transducer 21.

When the aspirator type operating instrument 70 and the aspirator type handpiece 30 are connected to the main apparatus 5 that includes the suction processing device 16, the suction parameters that indicate the existence of the suction process are stored as the probe output parameters in the storage unit (not shown) in the probe 70a of the aspirator type operating instrument 70. The suction applicability parameters that indicate the suction applicability are stored as the vibrator output parameters in the storage unit (not shown) in the aspirator type handpiece 30.

When the information reading unit 7 receives the vibrator output information S1 that includes the suction applicability parameters and the probe output Information S2 that includes the suction parameters, the information reading unit 7 transmits, to the CPU 9, the vibrator output information S1a, which is the vibrator output information S1 converted into digital forms, and the probe output Information S2a, which is the probe output Information S2 converted into digital forms. The CPU 9 calculates the control parameters based on the vibrator output information S1a and the probe output Information S2a, and stores the control parameters in the RAM 9a. The control parameters include the suction parameters.

The CPU 9 transmits the suction control signal S13 that corresponds to the suction parameters to the suction processing device 16, and controls the suction process to suck the emulsified target while supplying the perfusion solution to the target. The suction processing device 16 supplies the perfusion solution from the tip of the aspirator type operating instrument 70 through the water supply opening 16a and the water delivery tube 70d. The suction processing device 16 sucks the emulsified target and the perfusion solution from the tip of the probe 70a through the suction opening 16b, the suction tube 30d, and the opening 30e. Thus, the suction process is achieved.

The calculating process of the control parameters is explained in detail using the vibrator output parameters and the probe output parameters as examples. FIG. 7 is a table that of the probe output parameters that are stored in the storage unit 41. FIG. 8 is a table of the vibrator output parameters that are stored in the storage unit 23. FIG. 9 is a table of the control parameters calculated by the CPU 9 based on the probe output parameters and the vibrator output parameters.

Each of parameters #1, #2 shown in FIG. 7 corresponds to a different probe having different characteristics. The parameter #1 includes parameters of a probe that is attached to a scissors type operating instrument for an endoscope operation. The parameter #2 includes parameters of a probe that is attached to a scissors type operating instrument for a celiotomy operation. Each of parameters #3, #4 shown in FIG. 8 corresponds to a different handpiece having different characteristics. The parameter #3 includes parameters of a compact handpiece of high-frequency driving. The parameter #4 includes parameters of a large handpiece of high-frequency driving.

When the probe output parameters in the parameter #1 are stored in the storage unit 41, and the vibrator output parameters in the parameter #2 are stored in the storage unit 23, the information reading unit 7 receives the vibrator output information S1 that indicates the parameter #3 and the probe output Information S2 that indicates the parameter #1 from the storage unit 23, 41. Then the information reading unit 7 transmits the vibrator output information S1a and the probe output Information S2a, which are the vibrator output information S1 and the probe output Information S2 converted into predetermined digital codes, to the CPU 9. The CPU 9 calculates the control parameters based on the vibrator output information S1a and the probe output Information S2a. In this case, the CPU 9 obtains the control parameters in which the driving frequency is 47 kHz, and the voltage multiplying ratio parameter is 1:5, and the voltage rating is 150 volt (V), and the inductor parameter is 5 millihenrys (mH) based on each parameter such as the driving frequency (47 kHz), the voltage multiplying ratio parameter (1:5), the voltage rating (150 V), and the inductor parameter (5 mH) that are provided in the probe output information S2a, and each parameter such as the driving frequency (47 kHz), the voltage multiplying ratio parameter (1:5), the voltage raging (150 V), and the inductor parameter (5 mH) that are provided in the vibrator output information S1a. If the ultrasonic vibrations, for example, having 100 micrometer (μm) amplitude are desired to be output by the ultrasonic transducer 21, the CPU 9 obtains the control parameters in which the driving current parameter is 1.0 ampere (A) based on an amplitude magnification rate (10-fold) that is provided in the probe output Information S2a and a current amplitude rate (10 μm/A) that is provided in the vibrator output information S1a. The CPU 9 derives the control parameter that indicates no output modulation based on an output modulation parameter (no output modulation) provided in the probe output Information S2a, and derives the control parameter that indicates no suction process based on the suction parameter (no suction process) and a suction applicability parameter (no) that is provided in the vibrator output information S1a. The CPU 9 obtains the control parameters #1, #3 as a result of the calculating process.

When the probe output parameters in the parameter #1 are stored in the storage unit 41, and when the vibrator output parameters in the parameter #4 are stored in the storage unit 23, the information reading unit 7 receives both the vibrator output information S1 that includes the parameter #4 and the probe output Information S2 that includes the parameter #1 from the storage unit 23, 41. The information reading unit 7 then transmits the vibrator output information S1a and the probe output Information S2a to the CPU 9. The CPU 9 calculates the control parameters based on the vibrator output information S1a and the probe output Information S2a receive. In this case, the CPU 9 detects the abnormal combination based on the driving frequency (47 kHz) provided in the probe output Information S2a and the driving frequency (23.5 kHz) provided in the vibrator output information S1a, and executes the use prohibition process.

Furthermore, when the probe output parameters in the parameter #2 are stored in the storage unit 41, and when the vibrator output parameters in the parameter #3 are stored in the storage unit 23, the CPU 9 detects the abnormal combination based on the driving frequency (23.5 kHz) provided in the probe output Information S2a and the driving frequency (47 kHz) provided in the vibrator output information S1a, and executes the use prohibition process, as the case of the combination of the parameter #1 #4.

Moreover, when the probe output parameters in the parameter #2 are stored in the storage unit 41, and the vibrator output parameters in the parameter #4 are stored in the storage unit 23, the CPU 9 obtains the control parameters in which the driving frequency is 23.5 kHz, and the voltage multiplying ratio parameter is 1:5, and the value of the voltage rating is 150 V, and the inductor parameter is 5 mH based on each parameter of the driving frequency (23.5 kHz), the voltage multiplying ratio parameter (1:5), the value of the voltage rating (150 V), and the inductor parameter (5 mH) that are provided in the probe output Information S2a, and each parameter of the driving frequency (23.5 kHz), the voltage multiplying ratio parameter (1:5), the value of the voltage rating (150 V), and the inductor parameter (5 mH) that are provided in the vibrator output information S1a. If the ultrasonic vibrations, for example, having 100 micrometer (μm) amplitude are desired to be output by the ultrasonic transducer 21, the CPU 9 obtains the control parameters in which the driving current parameter is 0.5 A based on the amplitude magnification rate (10-fold) that is provided in the probe output Information S2a and the current amplitude rate (20 μm/A) that is provided in the vibrator output information S1a. The CPU 9 derives the control parameter that indicates no output modulation based on an output modulation parameter (no output modulation) provided in the probe output Information S2a, and derives the control parameter that indicates no suction process based on the suction parameter (no suction process) that is provided in the probe output Information S2a and a suction applicability parameter (no) that is provided in the vibrator output information S1a. The CPU 9 obtains the control parameters #2, #4 as a result of the calculating process.

Figure 10:
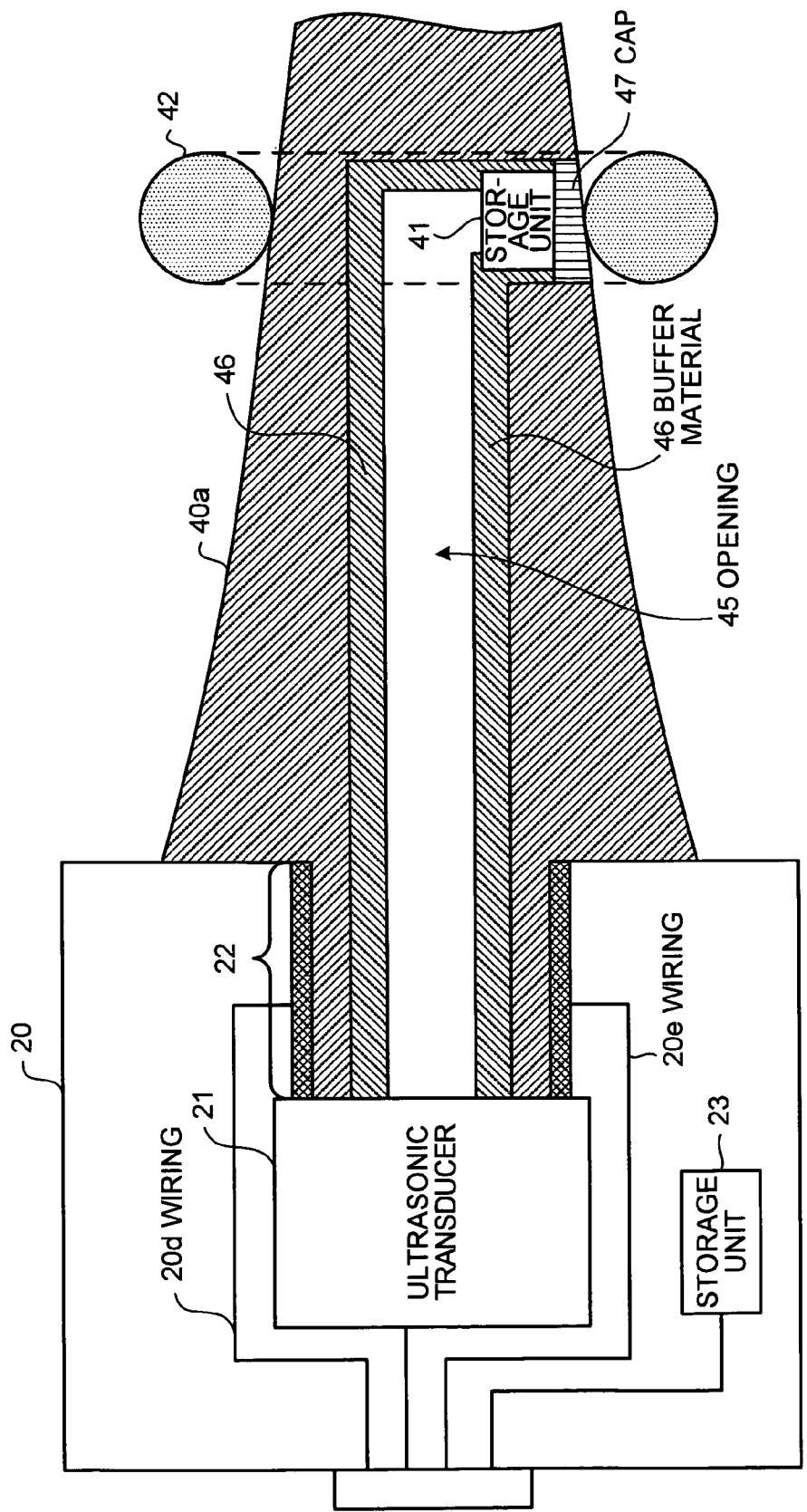
FIG. 10 is a schematic diagram for explaining a storage unit in a probe of an ultrasonic surgical system that is a variation of the first embodiment.

While in the first embodiment, a case of the storage unit 41 that is arranged near the center of the cross section of the probe has been exemplified, the present invention is not be limited to this case, and the storage unit 41 may be arranged near a sidewall of the probe. FIG. 10 is a schematic diagram for explaining a storage unit in a probe of an ultrasonic surgical system that is a variation of the first embodiment according to the present invention. The probe 40a includes an opening 45 and a buffer material 46. Moreover, the probe 40a includes a cap 47 to close the sidewall in which the storage unit 41 is arranged. Other components are the same as the components in the first embodiment, and like reference characters are given to like components.

The opening 45 is prepared between the sidewall of the probe 40a at which the seal material 42 is arranged and the end at which the fastening part 22 is arranged as shown in FIG. 10. It is preferable that the opening 45 is arranged near the center of the cross section of the probe 40a. This inhibits phenomena such as a deflection and a bend of the probe 40a caused by the ultrasonic vibrations, and reduces the damage to the probe 40a.

The buffer material 46 has almost the same functions and structure as the buffer material 44. The buffer material is arranged to cover the wall of the opening 45. The storage unit 41 is disposed at the sidewall of the probe 40a through the buffer material 46 as shown in FIG. 10. The cap 47 closes the sidewall at which the storage unit 41 is disposed. The buffer material 46 and the cap 47 hold the storage unit 41 at the sidewall so that the storage unit 41 can be replaced. The cap 47 may be detachably fixed by a fit between the cap and the sidewall, or with the seal material 42. The storage unit 41 is electrically connected to the wirings 20d, 20e through both a wiring (not shown) laid in the buffer material 46 and the fastening part 22.

The structure of the probe 40a in the variation of the first embodiment makes it easy to set the storage unit 41 in the probe 40a because the storage unit 41 can be disposed directly from outside of the sidewall. Furthermore, data input to the storage unit 41 and maintenance such as repair or replacement become easy. The same effect can be obtained for the probe 50a, 60a, and 70a that include the opening 45, the buffer material 46, and the cap 47.

While in the first embodiment and the variation of the first embodiment, a case of the buffer material that is arranged to cover the entire wall in the opening has been exemplified, the present invention is not to be limited to this case as long as the storage unit 41 is disposed through the buffer material in the probe 40a. Therefore, the buffer material should be arranged at least in the region at which the storage unit 41 is arranged. In this case, the storage unit 41 and the wirings 20d, 20e are electrically connected to each other through a wiring that includes an enamel wire, a flexible base, or the like. The wiring is prepared inside the opening.

While in the first embodiment and the variation of the first embodiment, a case of the screw electrode at the fastening part 22 that each functions as two signal lines to communicate information between the storage unit 41 and the main apparatus 5 has been exemplified, the present invention is not to be limited to this case, and each of the screw electrodes may function as a positive electrode and a negative electrode of the signal lines.

Furthermore, while in the first embodiment and the variation of the first embodiment, a case of that the storage unit 41 and the wirings 20e, 20e in the handpiece 20 are electrically connected through the screw electrodes at the fastening part 22, the present invention is not to be limited to this case. An electrode may be prepared on a contact surface at which the probe and the handpiece contact with each other. At least one of the wirings 20d, 20e may be electrically connected to the electrode. The storage unit 41 and at least one of the wiring 20d and the wiring 20e are electrically connected to each other through the electrode. The electrode and the storage unit 41 may be electrically connected to each other through the body of the probe or a wring prepared in the probe.

Moreover, while in the first embodiment, a case of combinations made up of two different types of the handpieces and two different types of the probes has been exemplified, the present invention is not to be limited to this case, and combinations made up of more than two different types of handpieces and more than two different types of probes maybe applied.

In the first embodiment, a storage unit is arranged in each of probes arranged to various operating instruments, and in a handpiece. Moreover, various kinds of parameters relating to the ultrasonic vibrations of the probe are stored in the storage unit in the probe, and various kinds of parameters relating to the ultrasonic vibrations of an ultrasonic transducer are stored in the storage unit in the handpiece. When an ultrasound output signal of a desirable values of a driving current and a driving voltage is to be output at a resonance frequency, control parameters are calculated based on the parameters in the storage units. The control parameters are written in the storage unit in the probe as updated information. Therefore, even if more than one probes are selectively connected to one handpiece, or even if more than one handpieces are selectively connected to one control apparatus, it is possible to drive the ultrasonic transducer efficiently at the resonance condition by instantly detecting the resonance frequency of the ultrasonic transducer. Thus, the versatility of the handpiece to the probe and the versatility of the control apparatus to the handpiece improve. Therefore, an ultrasonic surgical system with high versatility is realized with low cost. With the ultrasonic surgical system, an operator can perform various medical treatments efficiently because a trouble of exchanging devices during the operation is reduced. As a result, an operation time can also be shortened.

Furthermore, the structure of the probe 40*a* in the variation of the first embodiment makes it easy to set the storage unit 41 in the probe 40*a* because the storage unit 41 can be disposed directly from outside of the sidewall. Data input to the storage unit 41 and maintenance such as repair or replacement also become easy.

A second embodiment according to the present invention is explained below. While in the first embodiment, a storage unit is arranged in each of the probe and the handpiece, and the control parameters to control output of the desirable ultrasound output signal are calculated based on the parameters in each of the storage units, in the second embodiment, an identifier to identify a physical probe itself or a physical handpiece itself is prepared in each of the probe and the handpiece, and a control information storage unit that stores control parameters to control output of a desirable ultrasound output signal is prepared in a main apparatus. The control parameters corresponding to the probe and the handpiece are read from the control information storage unit.

Figure 11:
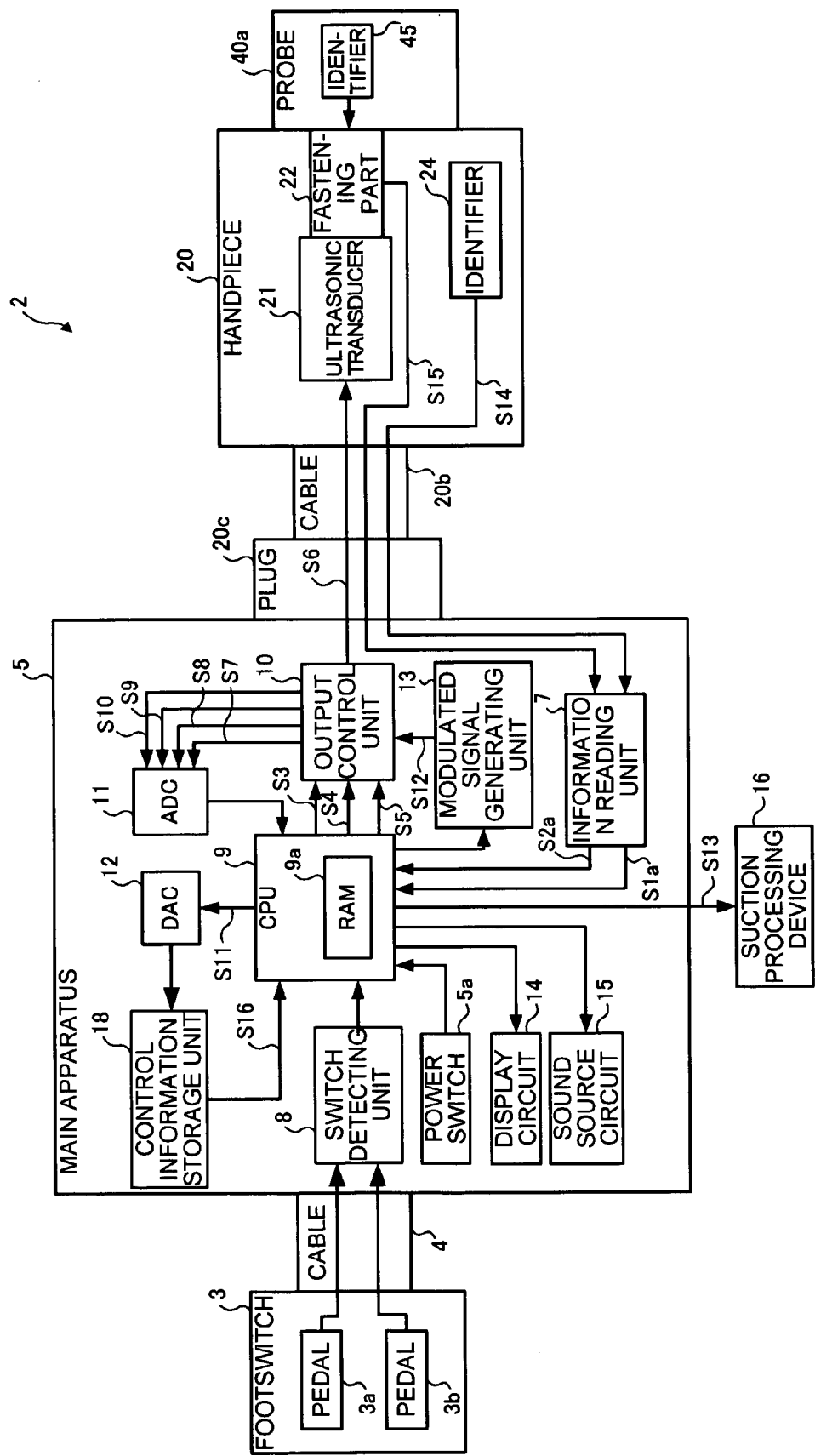
FIG. 11 is a block diagram of a system configuration of an ultrasonic surgical system according to a second embodiment of the present invention.

FIG. 11 is a block diagram of a system configuration of an ultrasonic surgical system according to a second embodiment of the present invention. An ultrasonic surgical system 2 includes identifiers 24, 45 instead of the storage units 23, 41 in the ultrasonic surgical system 1, and also includes a control information storage unit 18 in a main apparatus 5. Other components are the same as the components in the first embodiment, and like reference characters are given to like components.

The identifier 24 is realized with a resistance circuit, a nonvolatile memory such as a ROM, a barcode, or the like. When a handpiece 20 is electrically connected to the main apparatus 5, an information reading unit 7 reads handpiece identification information S14 to identify the handpiece from the identifier 24. If the identifier 24 is composed of the resistance circuit that includes a different resistance value for each of the handpiece, the information reading unit 7 detects the resistance value by an electrical conduction to the identifier 24, and reads the handpiece identification information S14. Because each of the handpiece has the different resistance value, the resistance value is the handpiece identification information S14 described above. If the identifier 24 is composed of the nonvolatile memory that stores the identification information of the handpiece, the information reading unit 7 reads the identification information from the identifier 24. The identification information is formed with combinations of alphanumeric characters and symbols. The identification information is an identification code each of the handpiece. The information reading unit 7 reads the identification information as the handpiece identification information S14. The case of the identifier 24 composed of the barcode is described later.

An identifier 45 is realized with a resistance circuit, a nonvolatile memory such as a ROM, a barcode, or the like. When a probe 40*a* is electrically connected to a main apparatus 5, the information reading unit 7 reads probe identification information S15 to identify the probe from the identifier 45. If the identifier 45 is composed of the resistance circuit that includes a different resistance value for each of the probe, the information reading unit 7 detects the resistance value by an electrical conduction to the identifier 45, and then reads the probe identification information S15. Because each of the probe has the different resistance value, the resistance value is the probe identification information S15 described above. If the identifier 45 is composed of the nonvolatile memory that stores the identification information to identify the probe, the information reading unit 7 reads the identification information from the identifier 45. The identification information is formed with combinations of alphanumeric characters and symbols. The identification information is an identification code of each of the probes. The information reading unit 7 reads the identification information as the probe identification information S15. The case of the identifier 45 composed of the barcode is described later.

The identifiers 24, 45 may be composed of the resistance circuit of the nonvolatile memory, or each of the identifiers 24, 45 may be composed of the resistance circuit or the nonvolatile memory. It is preferable that the identifier 45 is disposed in an opening 43 through a buffer material 44. Further, it is preferable that the identifier 45 is arranged near the center of the cross section of the probe 40*a*. The identifier 45 may be disposed in the opening 43 using a flexible base that is formed with a resin tape and the like.

A control information storage unit 18 is realized with a nonvolatile memory such as a ROM, preferably with a rewritable nonvolatile memory such as an EPROM or an EEPROM. In the control information storage unit 18, the control parameters are stored separately according to a combination of a handpiece and a probe. The CPU 9 detects the combination based on the handpiece identification information S14 and the probe identification information S15. The CPU 9 reads the control parameters that correspond to the combination from the control information storage unit 18. Thus, the CPU 9 matches each of the combination and each of the control parameters without fail.

The CPU 9 stores the control parameters in a RAM 9*a*. When the CPU 9 receives an instruction signal to start the output setting control from a switch detecting unit 8, the CPU 9 reads the control parameters from the RAM 9*a*, and transmits the control parameters to an output control unit 10. Thus, the output setting control is achieved. Moreover, the CPU 9 updates the control parameters by storing each of the parameters that are received from the output control unit 10 through the ADC 11 in the RAM 9*a*.

If the control information storage unit 18 is composed of a rewritable nonvolatile memory such as the EPROM and the EEPROM, it is possible to updates the control parameters. When the CPU 9 receives an instruction signal to stop the output setting control from the switch detecting unit 8, the CPU 9 transmits parameter update information S11 to a DAC 12 as updated information of the control parameters. The DAC 12 converts the parameter update information S11 into analog forms, and then, transmits to the control information storage unit 18 to update the control parameters that correspond to the combination of the handpiece and the probe. Thus, the control information storage unit 18 stores the latest parameters to achieve the ultrasonic vibrations at the resonance frequency.

The control information storage unit 18 may also be composed of a non-rewritable nonvolatile memory such as the ROM, and the update process of the control parameters described above may not to be carried out. In this case, it is possible to provide a new data of the control parameters by exchanging the nonvolatile memory disposed as the control information storage unit 18 regardless of a type of the nonvolatile memory.

As shown in FIG. 12, a type A is a probe that is arranged in a scissors type operating instrument for an endoscope operation, and that drives at a frequency of 47 kHz, and that does not require an output modulation, and that is not used in a suction process. A type B is a probe that is arranged in the hook type operating instrument for an endoscope operation, and that drives at a frequency of 47 kHz, and that does not require an output modulation, and that is not used in a suction process. A type C is a probe that is arranged in the scissors type operating instrument for a celiotomy operation, and that drives at a frequency of 23.5 kHz, and that does not require an output modulation, and that is not used in a suction process. A type D is a probe that is arranged in the aspirator type operating instrument, and that drives at a frequency of 23.5 kHz, and that is used in a suction process, and that does not require an output modulation. A type E is a probe that is arranged in the aspirator type operating instrument for a celiotomy operation, and that drives at a frequency of 23.5 kHz, and that is used in a suction process, and that does not require an output modulation. A type F is a probe that is arranged in the lithotrite type operating instrument for a celiotomy operation, and that drives at a frequency of 23.5 kHz, and that requires an output modulation, and that is not used in a suction process. As shown in FIG. 13, a type G is a handpiece that drives with a frequency of 23.5 kHz, and that is not applicable for a suction process. A type H is a handpiece that drives at a frequency of 47 kHz, and that is not applicable for a suction process. A type I is a handpiece that drives at a frequency of 23.5 kHz, and that is applicable for a suction process.

FIG. 14 is a table of control parameters correspond to each of the combination of the probe and the handpiece. The control parameters are stored in the control information storage unit 18. As shown in FIG. 14, the control parameters include data #1 to #18 corresponding to the combination.

The present invention is not to be limited to the types and the number of the combinations and the control parameters that are exemplified in the second embodiment. A desirable number of the control parameters according to a desirable number of the combinations may be stored. Thus, control parameters can be used corresponding to the desirable combinations further diversified.

The information reading unit 7 reads the probe identification information S15 to identify the probe that corresponds to one of the types A to F and the handpiece identification information S14 to identify the handpiece that corresponds to one of the types G to I from each of the identifiers. The CPU 9 reads the probe identification information S15 and the handpiece identification information S14 through the information reading unit 7. The CPU 9 detects the combination based on the handpiece identification information S14 and the probe identification information S15. The CPU 9 reads the control parameters that correspond to the combination from the control information storage unit 18. The control parameters to be read correspond to one of the data #1 to #8.

For example, when the handpiece of the type H and the probe of the type A are applied, the CPU 9 detects the combination based on the probe identification information S15 and the handpiece identification information S14 from each of the identifiers, and reads the control parameters of the data #2 that correspond to the combination from the control information storage unit 18. Then, the CPU 9 transmits the control parameters to the output control unit 10. Thus, the output setting control suitable for the combination is carried out. Similarly, the CPU 9 reads each of the data #5, #7, #9, #12, #15, #16, and #18 corresponding to each combination of the type B and the type H; the type C and the type G; the type C and the type I; type D and the type I; the type E and the type I; the type F and the type G; and the type F and the type I. Thus, the output setting control suitable for the combination is carried out.

When the combination meets one of the combinations of the type A and the type G; the type A and the type I; the type B and the type G; the type B and the type I; the type C and the type H; and the type F and the type F, the CPU 9 detects an abnormal combination due to the difference of the driving frequency. The CPU 9 executes a use prohibition process. Moreover, the combination meets any one of the combinations of the type D and the type G; the type D and the type H; the type E and the type G; and the type E and the type H, the CPU 9 detects an abnormal combination due to incompatibility indicated by the suction parameters and the suction applicability parameters. The CPU 9 executes the use prohibition process.

In the second embodiment, the information to identify a physical probe is read from the identifier in each of the probes, and the information to identify a physical handpiece is read from the identifier in the handpiece to which the probe is connected. Because the combination of the probe and the handpiece is detected based on the information read, and the control parameters are read corresponding to the combination thus detected, it is possible to read the control parameters suitable for the combination. Therefore, it is also possible to obtain the effect obtained in the first embodiment, and to realize the ultrasonic surgical system with simpler system with ease.

Figure 15:
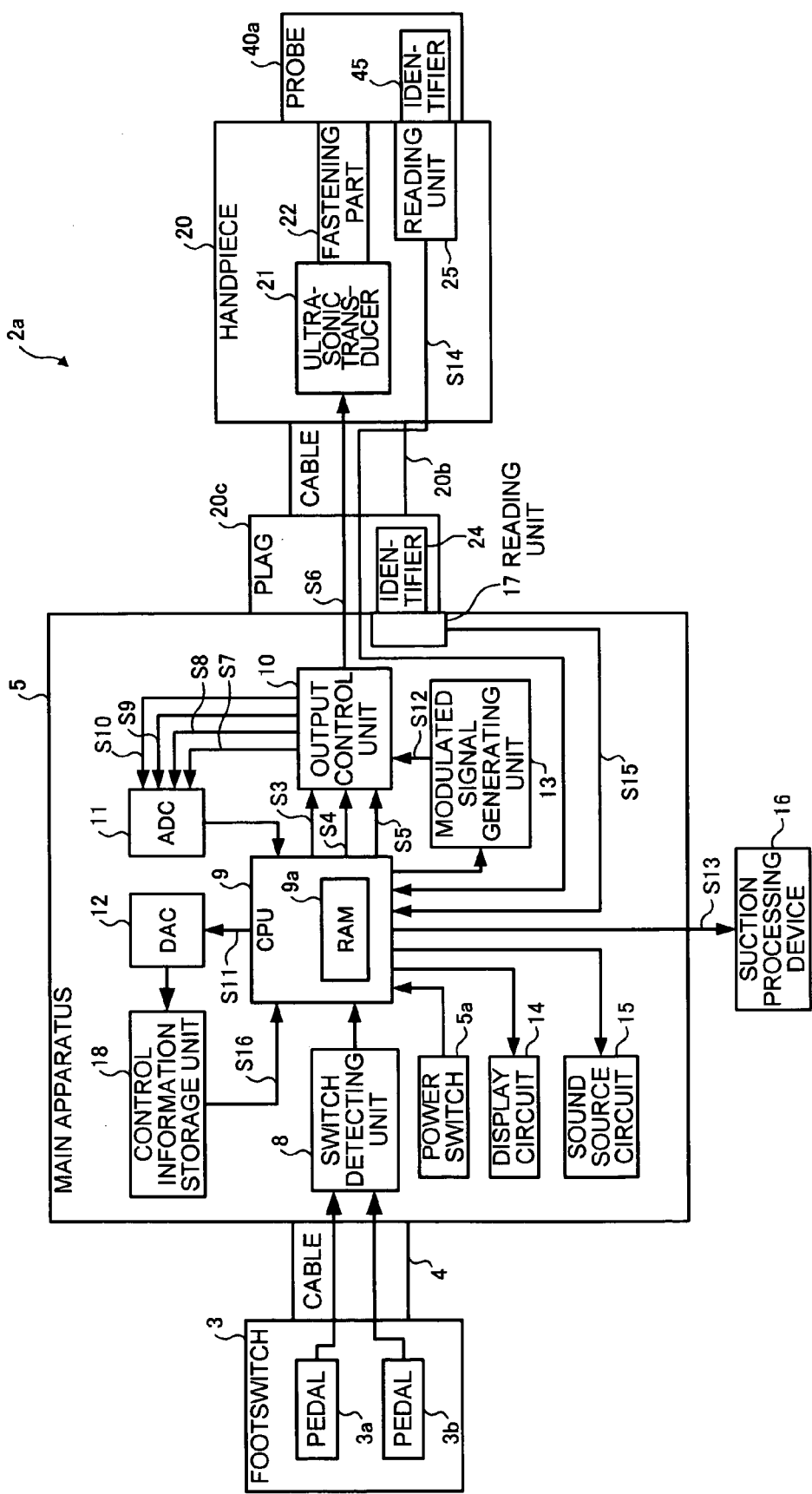
FIG. 15 is a block diagram of a system configuration of an ultrasonic surgical system that is a variation of the second embodiment according to the present invention.

The identifier 24 and the identifier 45 may be realized using a barcode. FIG. 15 is a block diagram of a system configuration of a variation of the ultrasonic surgical system 2 in the second embodiment. An ultrasonic surgical system 2*a* includes identifiers 24, 45 that are composed of the barcode, and includes reading units 17, 25 instead of the information reading unit 7. The reading units 17, 25 read the barcode. Other components are the same as the components in the first embodiment, and like reference characters are given to like components.

The reading unit 17 is realized with a well known barcode reader. The reading unit 17 is arranged so as to have a contact with a plug 20*c* in a handpiece 20 preferably at a connector 5*c* in a main apparatus 5. The identifier 24 is arranged in the plug 20*c* so as to touch the reading unit 17 when the plug 20*c* is plugged into the connector 5*c*. The reading unit 17 can read the barcode information in the identifier 24 under the control of a CPU 9 when the plug 20*c* is plugged into the connector 5*c*. The barcode information is read by the CPU 9 as the handpiece identification information S14.

The reading unit 25 is realized with the well-known barcode reader. The reading unit 25 is arranged in the handpiece 20 so as to have a contact with a probe 40*a* that is connected to the handpiece 20. The identifier 45 is arranged in a probe 40*a* so as to touch the reading unit 25 when the probe 40*a* is connected to the handpiece 20. The reading unit 25 can read the barcode information in the identifier 45 under the control of the CPU 9 when the probe 40*a* is connected to the handpiece 20 and the plug 20*c* is plugged into connector 5*c*. The barcode information is read by the CPU 9 as the probe identification information S15.

In the variation of the second embodiment, the reading units 17, 25 read the identification information of the probe and the handpiece that are included in the barcodes in the identifiers 24, 45 under the control of the CPU 9. This enables the CPU 9 to detect the combination of the probe and the handpiece to be applied. Therefore, the CPU 9 can read the control parameters suitable for the combination.

A third embodiment of the present invention is explained below. While in the first embodiment, the storage unit 41 is disposed inside the wall of the probe 40*a* through the buffer material 41, in the third embodiment, a supporting rod holds the storage unit 41 in a probe. The storage unit 41 is arranged at a portion that corresponds to a node of a standing wave in the probe without contact with the probe.

Figure 16:
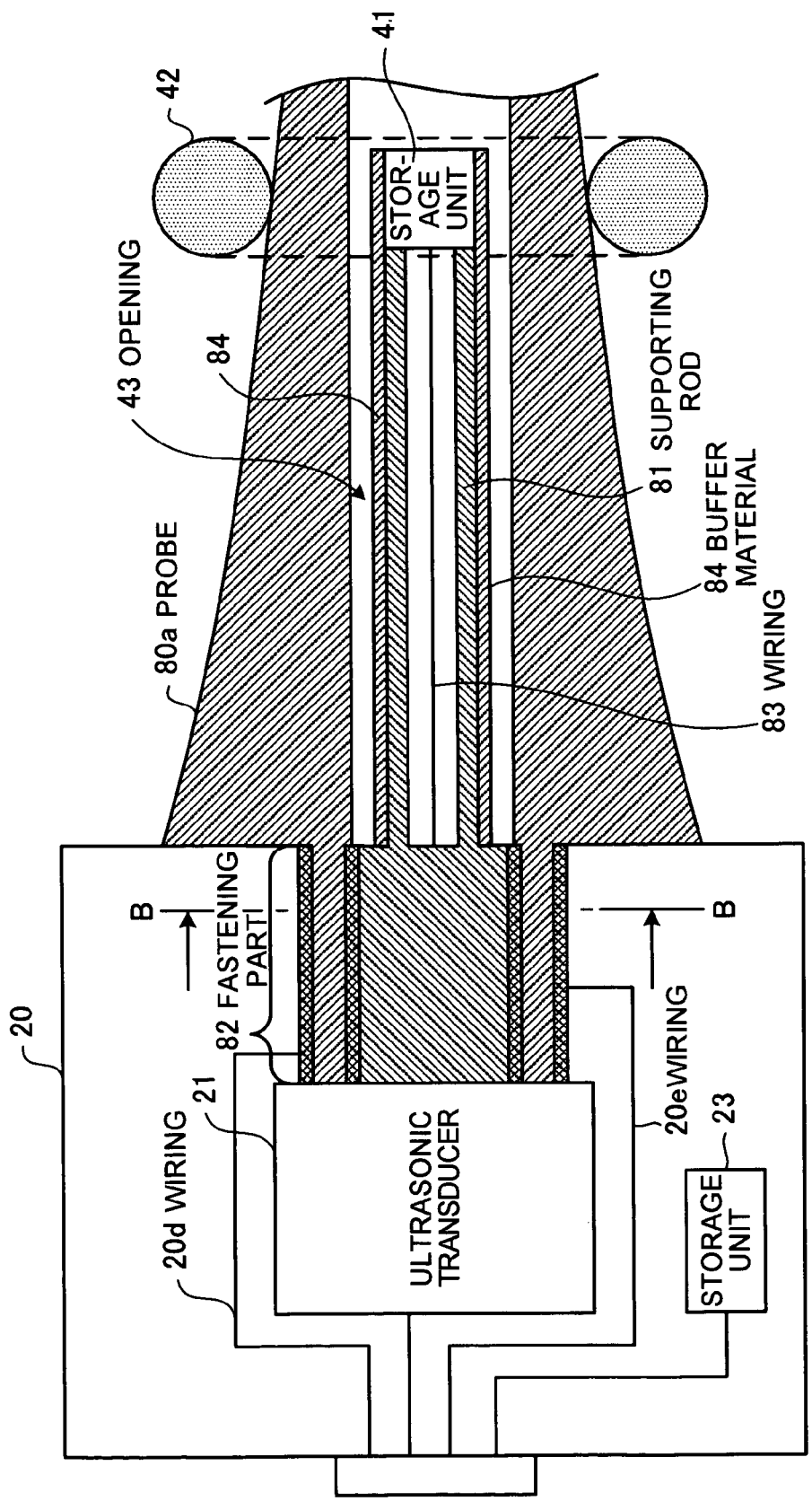
FIG. 16 is a schematic diagram for explaining condition of the probe and the handpiece that are connected to each other, and the disposition of a storage unit in an ultrasonic surgical system according to a third embodiment of the present invention.

FIG. 16 is a schematic diagram for explaining condition of the probe and the handpiece that are connected to each other, and disposition of a storage unit 41 in an ultrasonic surgical system according to a third embodiment of the present invention. As shown in FIG. 16, a probe 80*a* is connected to a handpiece 20 with screws. The probe 80*a* is connected to a fastening part 82. The probe 80*a* includes an opening 43. A supporting rod 81 holds the storage unit 41 at a tip in the opening 43 so that the storage unit 41 can be replaced. The supporting rod 81 is connected to the probe 80*a* with screws at the fastening part 82. A buffer material 84 covers around the supporting rod 81. Other components are the same as the components in the first embodiment, and like reference characters are given to like components. The probe 80*a* includes the scissors type operating instrument 40, the hook type operating instrument, the lithotrite type operating instrument 60 that are described above.

The supporting rod 81 is realized with a pipe shaped rod, and holds the storage unit 41 at the tip so that the storage unit 41 can be replaced. As described above, the buffer material 84 covers around the supporting rod 81. The buffer material 84 is formed with an elastic body such as a rubber or various kinds of resins such as of vinyl family or of urethane family. In this case, the maximum width of the cross section of the supporting rod 81 covered with the buffer material is smaller than the minimum width of the opening 43. This provides a clearance between the supporting rod 81 or the buffer material 84 and the probe 80*a*. Thus the supporting rod 81 or the storage unit 41 does not contact the probe 80*a*. This prevents damage to the storage unit 41 and a short circuit between the probe 80*a* and the supporting rod 81 or the storage unit 41. The clearance and the buffer material 84 also ease concentration of stress, to the storage unit 41, caused by the standing wave generated in the probe 40*a*.

The supporting rod 81 is arranged in the probe 80*a* in such a manner that the storage unit 41 at the tip is placed inside a seal material 42 as shown in FIG. 16. Thus, the storage unit 41 is arranged at the portion that corresponds to the node of the standing wave. This inhibits influence of vibrations generated by the standing wave to the storage unit 41 as much as possible, and thus prevents a malfunction such as damage of the storage unit 41 or a brake in a cable.

It is preferable that the supporting rod 81 is arranged in such a manner that the central axis in the direction of the length substantially meets the central axis in the direction of the length of the probe 80*a*. Thus the storage unit 41 is arranged near the center of the cross section of the probe 80*a*. This enables to prevent phenomena such as a deflection and a bend of the probe 80*a* and the supporting rod 81 caused by the ultrasonic vibrations, and damage to the probe 80*a*, the supporting rod 81, and the storage unit 41.

The supporting rod 81 includes a wiring 83 in a hollow of the pipe structure. The wiring 83 is formed with an enamel wire or a flexible base and the like. The wiring 83 electrically connects the storage unit 41 and the fastening part 82. The supporting rod 81 is insulated from the wiring 83. The body of the supporting rod 81 functions as another writing to electrically connect the storage unit 41 and the fastening part 82. Therefore, the storage unit 41 is electrically connected to the wiring 20*d* or the wiring 20*e* through the wiring 83 and the fastening part 82, and is electrically connected to the wiring 20*e* or the wiring 20*d* through the body of the supporting rod 81 and the fastening part 82. For example, the storage unit 41 is electrically connected to the wiring 20*d* through the body of the supporting rod 81 and the fastening part 82, and is electrically connected to the wiring 20*e* through the wiring 83 and the fastening part 82.

Figure 17:
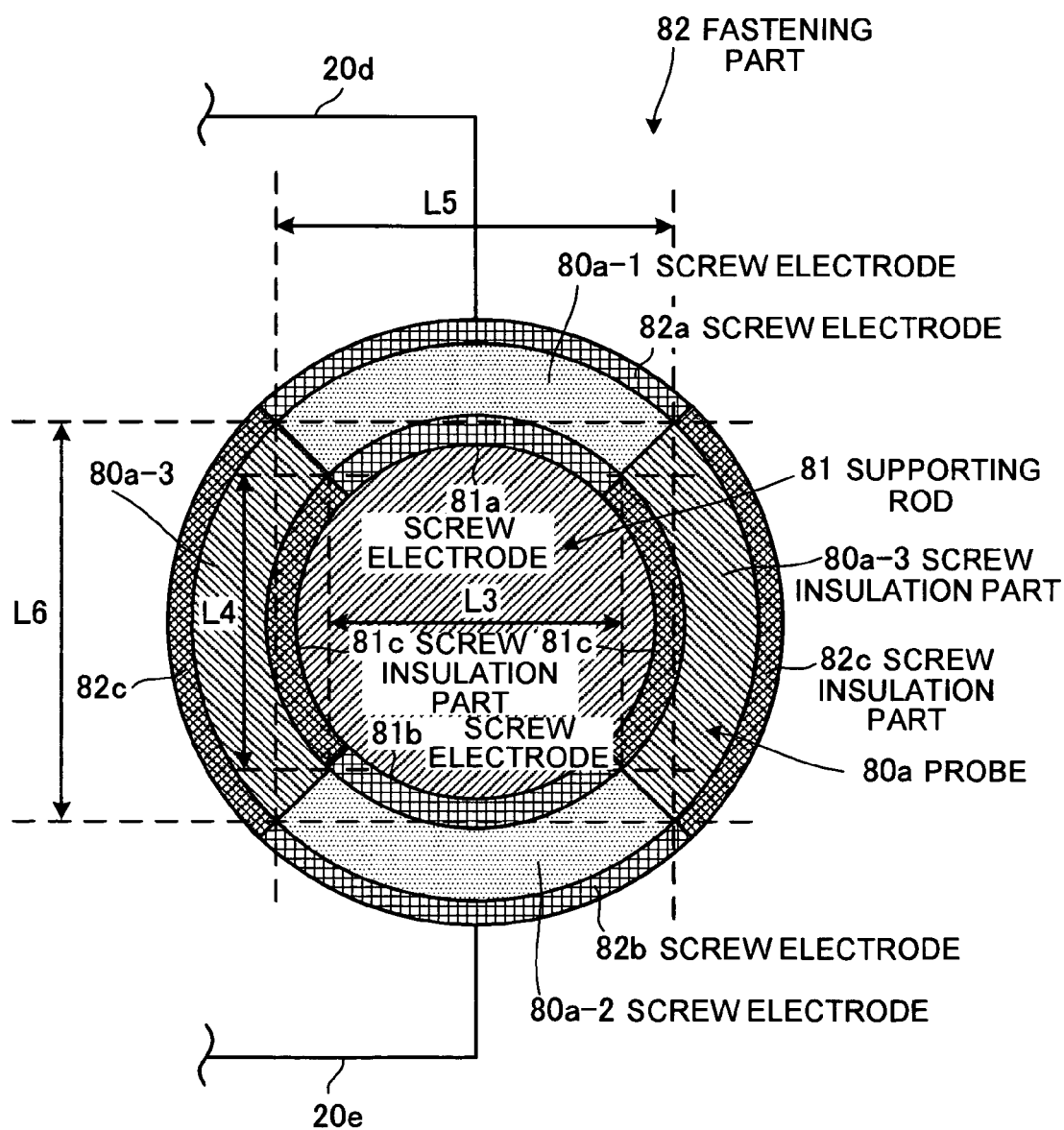
FIG. 17 is a schematic diagram of a fastening part taken along a line B-B shown in FIG. 16.

FIG. 17 is a schematic diagram of a fastening part taken along a line B-B shown in FIG. 16. As shown in FIG. 17, the fastening part 82 includes screw electrodes 81*a*, 81*b* and a screw insulation part 81*c* as screw parts of the supporting rod 81, screw electrodes 80*a*-1, 80*a*-2 and a screw insulation part 80*a*-3 as screw parts of the probe 80*a*, screw electrodes 82*a*, 82*b* and a screw insulation part 82*c* as screw parts of the handpiece 20. The supporting rod 81 and the probe 80*a* are connected to each other by fastening the screw parts of the supporting rod 81 and the screw parts of the probe 80*a* with screws. The probe 80*a* and the handpiece 20 are connected to each other by fastening the screw parts of the probe 80*a* and the screw parts of the handpiece 20 with screws.

The screw electrode 81*a* is insulated from the screw electrode 81*b* by the screw insulation part 81*c*. The screw electrode 80*a*-1 is insulated from the screw electrode 80*a*-2 by the screw insulation part 80*a*-3. The screw electrode 82*a* is insulated from the screw electrode 82*b* by the screw insulation part 82*c*. The storage unit 41 is electrically connected to each of the screw electrodes 81*a*, 81*b* through the body of the supporting rod 81 and the wiring 83 described above. For example, the storage unit 41 is electrically connected to the screw electrode 81*a* through the body of the supporting rod 81, and to the screw electrode 81*b* through the wiring 83. Each of the screw electrodes 82*a*, 82*b* is electrically connected to each of the wirings 20*e*, 20*e*. Therefore, when the supporting rod 81 is securely connected to the probe 80*a*, and when the probe 80*a* is securely connected to the handpiece 20, for example, the storage unit 41 is electrically connected to the wiring 20*d* through the body of the supporting rod 81, the screw electrode 81*a*, the screw electrode 80*a*-1, and the screw electrode 82*a*, and electrically connected to the wiring 20*e* through the wiring 83, the screw electrode 81*b*, the screw electrode 80*a*-2, and the screw electrode 82*b*. In this case, the screw electrodes 81*a*, 81*b*, the screw electrodes 80*a*-1, 80*a*-2, and the screw electrodes 82*a*, 82*b* function as two signal lines to communicate information between the storage unit 41 and the main apparatus 5 grounding to the earth.

The screw electrodes 81*a*, 81*b* and the screw electrodes 80*a*-1, 80*a*-2 are arranged in such a manner that the maximum width L3 of the screw electrodes 81*a* and 81*b* is smaller than the minimum width L4 of the screw electrodes 80*a*-1 and 80*a*-2. The screw electrodes 80*a*-1, 80*a*-2 and the screw electrodes 82*a*, 82*b* are arranged in such a manner that the maximum width L5 of the screw electrodes 80*a*-1 and 80*a*-2 is smaller than the minimum width L6 of the screw electrodes 82*a* and 82*b*.

Thus, the screw electrode 81*a* is electrically connected to the screw electrode 80*a*-1 without contacting with two of the screw electrodes 80*a*-1, 80*a*-2 at the same time. Similarly, the screw electrode 81*b* is electrically connected to the screw electrode 80*a*-2 without contacting with two of the screw electrodes 80*a*-1, 80*a*-2 at the same time. On the other hand, the screw electrode 80*a*-1 is electrically connected to the screw electrode 82*a* without contacting with two of the screw electrodes 82*a*, 82*b* at the same time. Similarly, the screw electrode 80*a*-2 is electrically connected to the screw electrode 82*b* without contacting with two of the screw electrodes 82*a*, 82*b* at the same time.

While in the third embodiment, a case of a buffer material that is arranged around the supporting rod 81 has been exemplified, the present invention is not to be limited to this case, and the buffer material may be arranged to cover the inner surface of the probe 80*a*.

Moreover, while in the third embodiment, a case of a screw electrode in which each of the screw electrodes functions as two signal lines to communicate information between the storage unit 41 and the main apparatus 5 has been exemplified, the present invention is not to be limited to this case, and each of the screw electrodes may be given functions as a positive and a negative electrode of the signal lines.

Furthermore, while in the third embodiment, a case of the storage unit 41 to be held at the tip of the supporting rod 81 has been exemplified, the present invention is not to be limited to this case, and the identifier 45 of the ultrasonic surgical system according to the second embodiment may be held at the tip of the supporting rod 81.

In the third embodiment, most of the components are same as the first embodiment. The storage unit 41 is held with the supporting rod 81, and arranged at the portion that corresponds to the node of the standing wave in the probe 80*a*. The supporting rod 81 is connected to the probe 80*a* with screws to maintain the arrangement of the storage unit 41. Therefore, it is possible to arrange the storage unit 41 at the portion that corresponds to the node of the standing wave with ease while obtaining substantially the same effect as the first embodiment. This enables a probe assembling to arrange the replaceable storage unit 41 at the portion that corresponds to the node of the standing wave with ease and with low cost. Moreover, because the storage unit 41 can easily be replaced, data input to the storage unit 41 and maintenance such as repair or replacement can easily be achieved. The effect obtained in the third embodiment can also be obtained with any probe that corresponds to any one of the scissors type operating instrument 40, the hook type operating instrument, and the lithotrite type operating instrument 60.

Furthermore, it is possible to obtain substantially the same effect as the third embodiment with the identifier 45 in the second embodiment by providing almost the same structure as the third embodiment. The identifier 45 is arranged at the tip of the supporting rod 81 instead of the storage unit 41. Thus, it is possible to assemble the probe to set the identifier 45 at the portion that corresponds to the node of the standing wave with ease and with low cost. Moreover, it is possible to carry out maintenance of the identifier 45 such as repair or replacement with ease.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. A probe connected to an ultrasonic transducer, transmitting ultrasonic vibrations output from the ultrasonic transducer to a treatment target, comprising:
    a storage unit storing a parameter relating to control of the ultrasonic transducer, arranged in a portion of the probe, the portion of the probe corresponding to a node of a standing wave produced by the ultrasonic transducer;
    an opening at least linking an end of the robe to which the ultrasonic transducer is connected and the portion of the probe corresponding to the node of the standing wave; and
    a holding unit that holds the storage unit in the opening at the node of the standing wave, wherein
    the holding unit includes a buffer material that is arranged in the opening to reduce stress to the storage unit caused by the ultrasonic vibrations.

2. The probe according to claim 1, wherein the holding unit holds the storage unit so that the storage unit can be replaced.

3. The probe according to claim 2, wherein
    the holding unit is a supporting rod holding the storage unit at a tip of the rod so that the storage unit can be replaced, and when the supporting rod inserted in the opening is fastened with screws to the probe, the storage unit is arranged in the probe without contact with the probe.

4. The probe according to claim 1, wherein the storage unit is disposed near a center of a cross-section of the probe.

\* \* \* \* \*